US007332586B2

(12) United States Patent
Franzen et al.

(10) Patent No.: US 7,332,586 B2
(45) Date of Patent: Feb. 19, 2008

(54) NANOPARTICLE DELIVERY VEHICLE

(75) Inventors: Stefan Franzen, Apex, NC (US); Daniel L. Feldheim, Cary, NC (US); Alexander G. Tkachenko, Raleigh, NC (US); Marisha L. Godek, Fort Collins, CO (US); Joseph A. Ryan, Raleigh, NC (US); Miles F. Anderson, deceased, late of Raleigh, NC (US); by Stefan Franzen, legal representative, Apex, NC (US)

(73) Assignee: North Carolina State University, Raleigh, NC (US)

(*) Notice: Subject to any disclaimer, the term of this patent is extended or adjusted under 35 U.S.C. 154(b) by 421 days.

(21) Appl. No.: 10/192,393

(22) Filed: Jul. 10, 2002

(65) Prior Publication Data

US 2003/0147966 A1 Aug. 7, 2003

Related U.S. Application Data

(60) Provisional application No. 60/304,236, filed on Jul. 10, 2001.

(51) Int. Cl.
| | |
|---|---|
| *C07K 17/00* | (2006.01) |
| *C07K 17/02* | (2006.01) |
| *C07K 17/06* | (2006.01) |
| *C07K 17/14* | (2006.01) |
| *A61K 9/14* | (2006.01) |

(52) U.S. Cl. ............... 530/402; 530/324; 530/326; 530/327; 424/491; 977/773

(58) Field of Classification Search ............. 424/494, 424/450, 190.1, 491; 530/391.7; 435/459, 435/287.2
See application file for complete search history.

(56) References Cited

U.S. PATENT DOCUMENTS

| | | | | |
|---|---|---|---|---|
| 4,501,726 | A | 2/1985 | Schröder et al. | 424/1.1 |
| 4,904,479 | A | 2/1990 | Illum | 424/490 |
| 5,178,882 | A | 1/1993 | Kossovsky et al. | 424/494 |
| 5,219,577 | A | 6/1993 | Kossovsky et al. | 424/494 |
| 5,460,830 | A | 10/1995 | Kossovsky et al. | 424/493 |
| 5,460,831 | A | 10/1995 | Kossovsky et al. | 424/493 |
| 5,462,750 | A | 10/1995 | Kossovsky et al. | 424/493 |
| 5,462,751 | A * | 10/1995 | Kossovsky et al. | 424/494 |
| 5,521,291 | A * | 5/1996 | Curiel et al. | 530/391.7 |
| 5,543,158 | A | 8/1996 | Gref et al. | |
| 5,620,708 | A | 4/1997 | Amkraut et al. | |
| 5,807,746 | A | 9/1998 | Lin et al. | 435/375 |
| 6,150,168 | A | 11/2000 | Woo et al. | 435/440 |
| 6,153,597 | A | 11/2000 | Blanche et al. | 514/44 |
| 6,274,552 | B1 | 8/2001 | Tamarkin et al. | 514/12 |

FOREIGN PATENT DOCUMENTS

| | | |
|---|---|---|
| WO | WO 98/56363 | 12/1998 |
| WO | WO 99/13719 | 3/1999 |
| WO | WO 02/42325 A2 | 5/2002 |

OTHER PUBLICATIONS

Akhlynina et al., "Adenoviruses Synergize with Nuclear Localization Signals to Enhance Nuclear Delivery and Photodynamic Action of Internalizable Conjugates Containing Chlorin E6," Int. J. Cancer: 81, 734-740 (1999).*
Dworetzky et. al., "The Effects of Variations in the Number and Sequence of Targeting Signals on Nuclear Uptake," The Journal of Cell Biology, vol. 197, Oct. 1988: 1279-1287.*
Kreuter et al. "Passage of peptides through the blood-brain barrier with colloidal polymer particles (nanoparticles)" Brain research 674 (1995) 171-174.*
Tkachenko et al.,"Cellular Trajectories of Peptide-Modified Gold Particle Complexes: Comparison of Nuclear Localization Signals and Peptide Transduction Domains," Bioconjugate Chem., (2004), 15, 482-490.*
Tkachenko et al., Multifunctional Gold Nanoparticle-Peptide Complexes for Nuclear Targeting, J. Am. Chem. Soc. 125, 4700-4701 (2003).*
Yoo et al., "Biodegradable nanoparticles containing doxorubicin-PLGA Conjugate for Sustained Release," Pharmaceutical Research vol. 16, No. 7, 1999.*
Zhang et al (Gene Therapy 6:171-181, 1999).*
European Office Action corresponding to 02802543.5 dated Feb. 6, 2006.
Official Action of the European Patent Office corresponding to application No. 02 802 543.5-2108 dated Jun. 9, 2006.
Wu and Wu, Receptor-mediated in Vitro Gene Transformation by a Soluble DNA Carrier System, *J. of Biological Chemistry* 262, No. 10:4429-4432 (Apr. 5, 1987).
*Laboratory Medicine* 20, No. 1:47-49 (Jan. 1989).
International Preliminary Examination Report for PCT/US02/21733, Mar. 29, 2004.

* cited by examiner

*Primary Examiner*—Mary E Mosher
(74) *Attorney, Agent, or Firm*—Jenkins, Wilson, Taylor and Hunt, P.A.

(57) ABSTRACT

A nanoparticle delivery vehicle, comprising a nanoparticle, an active agent and a nuclear localization signal and methods of modulating gene expression and protein expression employing the nanoparticle delivery vehicle. A representative method includes providing a nanoparticle delivery vehicle comprising a nanoparticle having a diameter of about 30 nm or less, an active agent and a nuclear localization signal; and contacting a target cell with the nanoparticle delivery vehicle, whereby an active agent is delivered to the nucleus of a target cell. Another representative method includes providing a nanoparticle delivery vehicle comprising a nanoparticle having a diameter greater than or equal to about 30 nm, an active agent and a nuclear localization signal; and contacting a target cell with the nanoparticle delivery vehicle, whereby an active agent is delivered to the cytoplasm of a cell.

26 Claims, 2 Drawing Sheets

SEQUENCE LISTING

<160> NUMBER OF SEQ ID NOS: 7

<210> SEQ ID NO 1
<211> LENGTH: 7
<212> TYPE: PRT
<213> ORGANISM: Homo sapiens

<400> SEQUENCE: 1

Pro Lys Lys Lys Arg Lys Val
1               5

<210> SEQ ID NO 2
<211> LENGTH: 16
<212> TYPE: PRT
<213> ORGANISM: Homo sapiens

<400> SEQUENCE: 2

Lys Arg Pro Ala Ala Ile Lys Lys Ala Gly Gln Ala Lys Lys Lys Lys
1               5                   10                  15

<210> SEQ ID NO 3
<211> LENGTH: 13
<212> TYPE: PRT
<213> ORGANISM: Simian virus 40

<400> SEQUENCE: 3

Cys Gly Gly Gly Pro Lys Lys Lys Arg Lys Val Gly Gly
1               5                   10

<210> SEQ ID NO 4
<211> LENGTH: 13
<212> TYPE: PRT
<213> ORGANISM: Unknown
<220> FEATURE:
<223> OTHER INFORMATION: Unknown adenovirus

<400> SEQUENCE: 4

Cys Gly Gly Phe Ser Thr Ser Leu Arg Ala Arg Lys Ala
1               5                   10

<210> SEQ ID NO 5
<211> LENGTH: 17
<212> TYPE: PRT
<213> ORGANISM: Unknown
<220> FEATURE:
<223> OTHER INFORMATION: Unknown adenovirus

<400> SEQUENCE: 5

Cys Lys Lys Lys Lys Lys Ser Glu Asp Glu Tyr Pro Tyr Val Pro
1               5                   10                  15

Asn

<210> SEQ ID NO 6
<211> LENGTH: 28
<212> TYPE: PRT
<213> ORGANISM: Unknown
<220> FEATURE:
<223> OTHER INFORMATION: Unknown adenovirus

<400> SEQUENCE: 6

Cys Lys Lys Lys Lys Lys Lys Ser Glu Asp Glu Tyr Pro Tyr Val
1               5                   10                  15

Pro Asn Phe Ser Thr Ser Leu Arg Ala Arg Lys Ala

```
                          20              25
<210> SEQ ID NO 7
<211> LENGTH: 4
<212> TYPE: PRT
<213> ORGANISM: Unknown
<220> FEATURE:
<223> OTHER INFORMATION: Unknown adenovirus
<220> FEATURE:
<221> NAME/KEY: misc_feature
<222> LOCATION: (1)..(4)
<223> OTHER INFORMATION: Xaa is any amino acid

<400> SEQUENCE: 7

Asn Pro Xaa Tyr
1
```

NANOPARTICLE DELIVERY VEHICLE

CROSS REFERENCE TO RELATED APPLICATIONS

This application is based on and claims priority to U.S. Provisional Patent Application Ser. No. 60/304,236, filed Jul. 10, 2001, herein incorporated by reference in its entirety.

GRANT STATEMENT

This work was supported by NSF grants NSF-DMR (9900073) and NSF-MDB (9874895). Thus, the U.S. Government has certain rights in the invention.

TECHNICAL FIELD

The present invention relates to compositions for and methods of delivering an active agent to and into cells. More particularly, the method employs a nanoparticle delivery vehicle as a vehicle for carrying proteins, nucleic acids, protein and nucleic acid analogs, small molecules and other compounds to the surface of a cell, into the cytoplasm of a cell or into a cell's nucleus.

Table of Abbreviations

| | |
|---|---|
| ATP | adenosine triphosphate |
| ADP | adenosine diphosphate |
| AS | antisense |
| AS-ODN | antisense oligodeoxynucleotides |
| bipy | bipyridine |
| cDNA | complementary DNA |
| DNA | deoxyribonucleic acid |
| dsDNA | double stranded DNA |
| EDTA | ethylenediaminetetraacetic acid |
| HEPES | N-2-hydroxyethylpiperazine-N'-2-ethanesulfonic acid |
| ITO | indium tin oxide |
| IV | intravenous |
| kDa | kilodalton(s) |
| LB | Luria broth |
| MES | 2-[N-Morpholino]ethanesulfonic acid |
| mRNA | messenger RNA |
| NDP | nucleotide diphosphate |
| NLS | nuclear localization signal |
| nt | nucleotide |
| NTP | nucleotide triphosphate |
| ODN | oligodeoxynucleotide |
| PACVD | plasma-assisted chemical vapor deposition |
| PAGE | polyacrylamide gel electrophoresis |
| PBS | phosphate buffered saline |
| PCR | polymerase chain reaction |
| pI | isoelectric point |
| PNA | peptide nucleic acid analog |
| RES | reticuloendothelial system |
| RME | receptor mediated endocytosis |
| RNA | ribonucleic acid |
| SDS | sodium dodecyl sulfate |
| SDS-PAGE | sodium dodecyl sulfate polyacrylamide gel electrophoresis |
| ssDNA | single stranded DNA |
| TEM | transmission electron microscopy |

Amino Acid Abbreviations

| Single-Letter Code | Three-Letter Code | Name |
|---|---|---|
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

BACKGROUND ART

The development of new forms of therapeutics that use macromolecules such as proteins or nucleic acids as therapeutic agents has created a need to develop new and effective approaches of delivering such macromolecules to their appropriate cellular targets. Therapeutics based on either the use of specific polypeptide growth factors or specific genes to replace or supplement absent or defective genes are examples of therapeutics that might require such new delivery systems. Therapeutics involving oligonucleotides that interact with DNA to modulate the expression of a gene or other segment of DNA might also require a new delivery system. Clinical application of such therapies depends not only on the reliability and efficiency of new delivery systems but also on their safety and on the ease with which the technologies underlying these systems can be adapted for large-scale pharmaceutical production, storage, and distribution of the therapeutic formulations.

Gene therapy has become an increasingly important mode of treating various genetic disorders. The potential for providing effective treatments, has stimulated an intense effort to apply this technology to diseases for which there have been no effective treatments. Recent progress in this area has indicated that gene therapy can have a significant impact not only on the treatment of single gene disorders, but also on other more complex diseases such as cancer. However, a significant obstacle in the attainment of efficient gene therapy regime has been the difficulty of designing new and effective approaches for delivering therapeutic nucleic acids to cells and intracellular targets. Indeed, an ideal vehicle for the delivery of nucleic acids or proteins into cells and tissues should be highly efficient, safe to use, easy to produce in large quantity and have sufficient stability to be practicable as a pharmaceutical delivery vehicle.

When nucleic acids are used as "active agents" in a gene therapy regime, there are essentially two systems based on viral vectors or nonviral vectors that are described in the art: (1) retro, adeno and herpes viruses (or their recombinants) are presently being studied in vivo as viral vectors; and (2) liposomes and ligands of cell surface-specific receptors are being researched in vivo as nonviral vectors (Wu & Wu, (1991) *Biotherapy* 3: 87-95; Ledley, (1993) *Clin. Invest. Med.* 16: 78-88). Nanocrystalline particles are also being investigated (U.S. Pat. No. 5,460,831 to Kossovsky). All of these approaches suffer from a variety of disadvantages, including undesired in vivo degradation and a lack of specificity for a given target structure, for example, the nucleus of a cell or the surface of a cell expressing a particular type of structure.

Nanoparticle technology has found application in a variety of disciplines, but has found minimal application in pharmacology and drug delivery. The development of therapeutic nanoparticles was first attempted around 1970, and the proposed nanoparticles were intended to function as carriers of anticancer and other drugs (Couvreur et al., (1982) *J. Pharm. Sci.*, 71: 790-92). Attempts were also made to elucidate methods by which the uptake of the nanoparticles by the cells of the reticuloendothelial system (RES) would be minimized (Couvreur et al., (1986) in *Polymeric Nanoparticles and Microspheres*, (Guiot & Couvreur, eds.), CRC Press, Boca Raton, pp. 27-93). Other attempts pursued the use of nanoparticles for treatment of specific disorders. See, e.g., Labhasetwar et al., (1997) *Adv. Drug. Del. Rev.*, 24: 63-85.

Although nanoparticles have shown promise as useful tools for drug delivery systems, many problems remain. Some unsolved problems relate to the control, selection, and behavior of various particle sizes, as well as problems surrounding the loading of particles with therapeutics. Additionally, the targeting of the nanoparticle to the appropriate cellular site has remained problematic. The design and provision of a nanoparticle delivery vehicle that addresses these problems thus represents and ongoing and long-felt need in the art.

SUMMARY OF THE INVENTION

A nanoparticle delivery vehicle is disclosed. In one embodiment, the nanoparticle delivery vehicle comprises: (a) a nanoparticle; (b) an active agent; and (c) a nuclear localization signal. In another embodiment, the nanoparticle delivery vehicle comprises (a) a plurality of targeting agents; (b) a nanoparticle scaffold; and (c) an active agent.

Preferably, the active agent is selected from the group consisting of double stranded nucleic acids, single stranded nucleic acids, chemically modified nucleic acids, peptide nucleic acids, proteins and small molecules. Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

Optionally, the nanoparticle delivery vehicle can further comprise two or more different active agents. Also optionally, the nanoparticle delivery vehicle can further comprise a biocompatibility-enhancing agent. As a further option, the nanoparticle delivery vehicle can further comprise a protective coating covering at least part of the delivery vehicle. In one embodiment, the protective coating can cover the entire delivery vehicle, including the active agent(s) and targeting agent(s). The protective coating can comprise a polymer. The protective coating can also comprise a biological material. The biological material can be a protein, lipid, carbohydrate, or combination thereof.

A method of delivering an active agent to the nucleus of a cell is disclosed. The method comprises:(a) providing a nanoparticle delivery vehicle of the present invention comprising a nanoparticle having a diameter of about 30 nm or less; and (b) contacting a target cell with the nanoparticle delivery vehicle, whereby an active agent is delivered to the nucleus of a target cell. Preferably, the active agent is selected from the group consisting of double stranded nucleic acids, single stranded nucleic acids, chemically modified nucleic acids, peptide nucleic acids, proteins and small molecules. Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

A method of delivering an active agent to the cytoplasm of a cell is disposed. The method comprises: (a) providing a nanoparticle delivery vehicle of the present invention comprising a nanoparticle having a diameter greater than or equal to about 30 nm; and (b) contacting a target cell with the nanoparticle delivery vehicle. Preferably, the active agent is selected from the group consisting of double stranded nucleic acids, single stranded nucleic acids, chemically modified nucleic acids, peptide nucleic acids, proteins and small molecules. Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

A method of modulating the expression of a target nucleic acid sequence is disclosed. The method comprises:(a) providing a nanoparticle delivery vehicle of the present invention comprising an active agent capable of interacting with a target nucleic acid sequence whose expression is to be modulated; (b) contacting a target cell comprising a target nucleic acid sequence with the nanoparticle delivery vehicle; and (c) modulating the expression of the target nucleic acid sequence through the contacting of step (b). Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

A method of modulating the expression of a target protein is disclosed. The method comprises: (a) providing a nanoparticle delivery vehicle of the present invention comprising a single stranded antisense nucleic acid sequence complementary to a nucleic acid sequence encoding a target protein; (b) contacting a target cell comprising a nucleic acid sequence encoding a target protein with the nanoparticle delivery vehicle; and (c) modulating the expression of the target protein through the contacting of step (b). Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

A method of modulating transcription in a sample is disclosed. The method comprises: (a) providing a nanoparticle delivery vehicle of the present invention comprising an active agent comprising a ligand for which a wild-type transcription component has greater affinity than a natural ligand of the wild-type transcription component; (b) contacting a sample comprising the wild-type transcription component with the nanoparticle delivery vehicle; and (c) modulating transcription in the sample through the contacting of step (b). Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

A method of modulating RNA splicing in a sample is disclosed. The method comprises: (a) providing a nanoparticle delivery vehicle of the present invention comprising a nucleic acid sequence known or suspected to alter the splicing pattern for a target gene; and (b) contacting a sample comprising the target gene with the nanoparticle delivery vehicle; and (c) modulating RNA splicing in a sample through the contacting of step (b). Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

A method of modulating the translation of an mRNA sequence encoding a protein of interest is disclosed. The method comprises: (a) providing a nanoparticle delivery vehicle of the present invention comprising a single stranded nucleic acid sequence complementary to a nucleic acid sequence of an mRNA sequence encoding a protein of interest; (b) contacting a sample comprising the mRNA sequence encoding a protein of interest with the nanoparticle delivery vehicle; and (c) modulating the translation of an mRNA sequence encoding a protein of interest through the contacting of step (b). Preferably, the nanoparticle delivery vehicle further comprises a tether sequence attached to, and disposed between, the active agent and the nanoparticle. Preferably, the nanoparticle delivery vehicle further comprises a cell surface recognition sequence. Preferably, the nanoparticle delivery vehicle is disposed in a pharmaceutically acceptable diluent. Preferably, the nanoparticle delivery vehicle further comprises a detectable moiety.

Accordingly, it is an object of the present invention to provide a nanoparticle delivery vehicle. This and other objects are achieved in whole or in part by the present invention.

Some of the objects of the invention having been stated hereinabove, other objects will be evident as the description proceeds, when taken in connection with the accompanying Drawings as best described hereinbelow.

DETAILED DESCRIPTION OF THE INVENTION

Figure 1A:
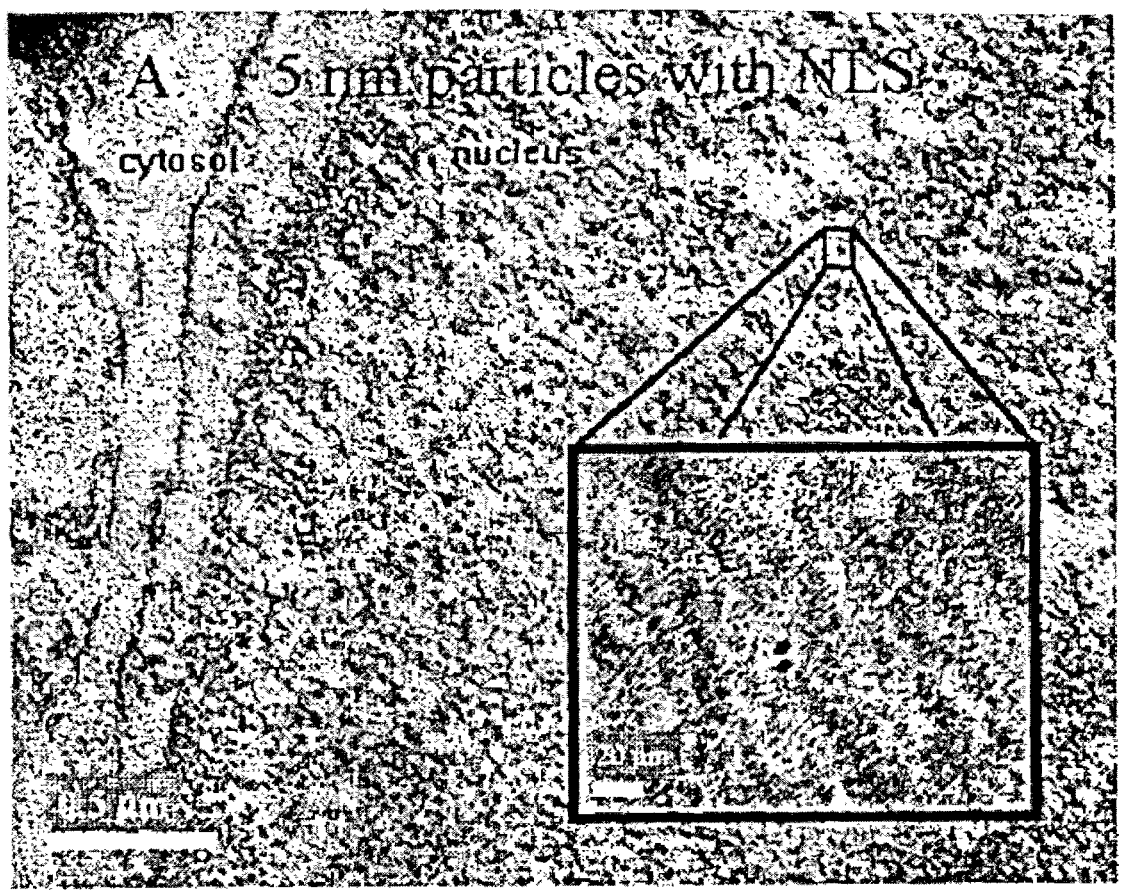
FIG. 1A is a transmission electron micrograph of hepatocytes grown in a medium comprising 5 nm nanoparticles. A region of the nucleus is highlighted in the inset.

The present invention provides a nanoparticle delivery vehicle as a vehicle for carrying proteins, nucleic acids, protein and nucleic acid analogs, small molecules and other compounds to the surface of a cell, into the cytoplasm of a cell and/or into a cell's nucleus. A plurality of sequences can be associated with a nanoparticle delivery vehicle, preferably a plurality of different sequences, such as RME sequences and NLS sequences. These sequences can aid in the translocation of a vehicle across various membranes, such as the nuclear membrane of a cell or the outer membrane of a cell. Thus, if membranes and other structures that generally inhibit translocation of a vehicle to a given location in or on a cell are analogized as "locks", NLS and RME sequences can be analogized to be "keys". Thus, in a preferred embodiment, a nanoparticle delivery vehicle of the present invention can comprise a plurality of different sequences or "keys," which can enable a given nanoparticle delivery vehicle to pass through various potential barriers to translocation in a variety of different cell types.

I. Definitions

Following long-standing patent law convention, the terms "a" and "an" mean "one or more" when used in this application, including the claims.

As used herein, the term "active agent" means a therapeutic agent, including but not limited to chemotherapeutic agents, radiotherapeutics, or radiosensitizing agents; an imaging agent; a diagnostic agent; or other agent known to interact with an intracellular protein, a nucleic acid or a soluble or insoluble ligand.

As used herein, the term "amino acid sequence" means an oligopeptide, peptide, polypeptide, or protein sequence, and fragments thereof, and naturally occurring or synthetic molecules. Where "amino acid sequence" is recited herein to refer to an amino acid sequence of a synthetic peptide or a naturally occurring protein molecule, amino acid sequence, and the like. The term is not meant to limit the amino acid sequence to a complete, native amino acid sequence associated with a recited protein molecule, but is intended to encompass variations on the native amino acid sequence as well.

As used herein, the term "biodegradable" means any structure, including but not limited to a nanoparticle, which decomposes or otherwise disintegrates after prolonged exposure to physiological conditions. To be biodegradable, the structure should be substantially disintegrated within a few weeks after introduction into the body. Brushite is a preferred biodegradable nanoparticle material.

As used herein, the terms "extracellular targeting agent" and "cell surface recognition sequence" are used interchangeably and refer to a small molecule or protein sequence that is recognized and bound by one or more receptors present on the surface of a particular cell. Cell surface recognition sequences can include HIV coat proteins (gp160, 41, 120) corona virus coat proteins, EBV coat proteins (gp350) and peptides. Other representative, but non-limiting cell surface recognition sequences can comprise carbohydrate and lipid, carbohydrates, peptide nucleic acids, morpholino oligonucleotides and polymers. It is intended that the term "cell surface recognition sequence" encompass any sequence or molecule recognized and/or bound by a cell surface receptor. It is preferable, but not required, that a "cell surface recognition sequence" that is recognized and/or bound by a cell surface receptor leads to receptor-mediated endocytosis (RME). A list of representative moieties that can be employed as targeting agents for internalization by RME is presented in Table 1.

As used herein, the term "chemical modification" means alteration of a first moiety by covalently, noncovalently or ionically binding a second moiety to the first moiety. Chemical modification can involve the addition of a detectable moiety to a peptide or protein.

As used herein, the term "detecting" means confirming the presence of a target entity by observing the occurrence of a detectable signal, such as an electrical, radiological or spectroscopic signal that will appear exclusively in the presence of the target entity. The term encompasses the use of electrophoresis techniques and blotting techniques, including northern, Southern, western and far western blots. The term "detecting" also includes the use of microscopy techniques, such as transmission electron microscopy. "Detecting" an event or the presence of a compound can be done directly or indirectly, for example, by monitoring the rate of transcription to detect the presence of transcription factors. Thus, the term "detecting" broadly means identifying the presence or absence of an event, compound, molecule, etc.

As used herein, the term "gene" is used for simplicity and means a functional protein, polypeptide or peptide encoding unit. As will be understood by those in the art, this functional term includes both genomic sequences and cDNA sequences.

As used herein, the term "gold" means element 79, which has the chemical symbol Au; the term specifically excludes any connotation related to color or other colorimetric properties.

As used herein, the term "homology" means a degree of complementarity. There can be partial homology or complete homology (i.e., identity). A partially complementary sequence that at least partially inhibits an identical sequence from hybridizing to a target nucleic acid can be considered "substantially homologous". The inhibition of hybridization of the completely complementary sequence to the target sequence can be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding can be tested by the use of a second target sequence that lacks even a partial degree of complementarity (e.g., less than about 30% identity). In the absence of non-specific binding, the probe will not hybridize to the second non-complementary target sequence.

As used herein, the term "hybridization" means the binding of a probe sample to a target sample. The probe sample can comprise a molecule to which a detectable moiety has been bound, thereby making it possible to detect the presence or absence of a probe sample.

As used herein, the term "interact" means detectable interactions between molecules, such as can be detected using, for example, transmission electron microscopy or fluorescence microscopy. The term "interact" is also meant to include "binding" interactions between molecules. Interactions can be, for example, nucleic acid-nucleic acid, protein-protein or protein-nucleic acid in nature.

As used herein, the term "isolated" means oligonucleotides substantially free of other nucleic acids, proteins, lipids, carbohydrates or other materials with which they can be associated, such association being either in cellular material or in a synthesis medium. The term can also be applied to polypeptides, in which case the polypeptide will be substantially free of nucleic acids, carbohydrates, lipids and other undesired polypeptides.

As used herein, the term "labeled" means the covalent, noncovalent or ionic attachment of a moiety capable of detection by electrochemical, spectroscopic, radiologic or other methods to a probe molecule.

As used herein, the term "modified" means an alteration from an entity's normally occurring state. An entity can be modified by removing discrete chemical units or by adding discrete chemical units. The term "modified" encompasses detectable labels as well as those entities added as aids in purification. Any variation from the normally occurring state, regardless of degree, is encompassed by the term "modified".

As used herein, the term "modulate" means an increase, decrease, or other alteration of any, or all, chemical and biological activities or properties of a sample which are mediated by a nucleic acid sequence, a peptide or a small molecule. The term "modulation" as used herein refers to both upregulation (i.e., activation or stimulation) and downregulation (i.e. inhibition or suppression) of a response or property.

As used herein, the term "mutation" carries its traditional connotation and means a change, inherited, naturally occurring or introduced, in a nucleic acid or polypeptide sequence, and is used in its sense as generally known to those of skill in the art.

As used herein, the terms "nano", "nanoscopic" "nanometer-sized", "nanostructured", "nanoscale", "DNA-nanoparticle complexes" and grammatical derivatives thereof are used synonymously and interchangeably and mean nanoparticles, nanoparticle composites and hollow nanocapsules less than or equal to about 1000 nanometers (nm) in diameter, preferably less than about 30 nanometers in diameter and more preferably less than about 10 nanometers in diameter. A nanoparticle can be fashioned from any material. A preferred nanoparticle is fashioned of a semiconductor material or metal, and more preferably of gold, $TiO_2$ or gold or $TiO_2$-containing materials. Biodegradable materials are also preferred, e.g. polypeptides. The terms can refer not only to the metal component of a nanoparticle, but the composite of metal and other component parts as well.

The term "nanoparticle" as used herein denotes a carrier structure which is biocompatible with and sufficiently resistant to chemical and/or physical destruction by the environment of use such that a sufficient amount of the nanoparticles remain substantially intact after injection into the blood stream, given intraperitoneally or orally or incubated with an in vitro sample so as to be able to reach the nucleus of a cell or some other cellular structure. If the drug can enter the cell in the form whereby it is adsorbed to the nanoparticles, the nanoparticles must also remain sufficiently intact to enter the cell. Biodegradation of the nanoparticle is permissible upon entry of a cell's nucleus. Nanoparticles can be solid colloidal particles ranging in size from 1 to 1000 nm. Nanoparticle can have any diameter less than or equal to 1000 nm, including 5, 10, 15, 20, 25, 30, 50, 100, 500 and 750 nm. Drugs, active agents, bioactive or other relevant materials can be incubated with the nanoparticles, and thereby be adsorbed or attached to the nanoparticle.

As used herein, the term "nanoparticle metal component" means a component of a nanoparticle delivery vehicle of the present invention to which a nuclear localization signal, drugs, bioactive and other relevant materials are bound. Typically, but not necessarily, the nanoparticle metal component comprises an approximately spherical metal atom-comprising entity. Preferably the nanoparticle metal component is an elemental metal or semiconductor material, such as a gold or $TiO_2$ particle.

As used herein, the term "nuclear localization signal" means an amino acid sequence known to, in vivo, direct a protein disposed in the cytoplasm of a cell across the nuclear membrane and into the nucleus of the cell. A nuclear localization signal can also target the exterior surface of a cell. Thus, a single nuclear localization signal can direct the entity with which it is associated to the exterior of a cell and to the nucleus of a cell. Such sequences can be of any size and composition, for example more than 25, 25, 15, 12, 10, 8, 7, 6, 5 or 4 amino acids, but will preferably comprise at least a four to eight amino acid sequence known to function as a nuclear localization signal (NLS).

As used herein, the term "pharmaceutically acceptable" and grammatical variations thereof, as it refers to compositions, carriers, diluents and reagents, means that the materials are capable of administration to or upon a vertebrate subject without the production of undesirable physiological effects such as nausea, dizziness, gastric upset, fever and the like.

As used herein, the terms "polypeptide", "protein", "gene product" and "peptide" are used interchangeably and mean any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product.

As used herein, the term "sequencing" means determining the ordered linear sequence of nucleic acids or amino acids of a DNA or peptide (or protein) target sample, using manual or automated laboratory techniques known in the art.

As used herein, the term "small molecule" means a molecule that has a molecular weight of less than or equal to 5000 daltons.

As used herein, the term "substantially pure" means that the polynucleotide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

As used herein, the term "targeting agent" means any agent having the ability to direct a moiety associated with the targeting agent to the surface of a cell, to the surface of a particular type of cell, or to the nucleus of a cell. A targeting agent can comprise, but is not limited to, proteins, peptides, small molecules, oligonucleotides, morpholino oligonucleotides and peptide nucleic acids. A targeting can be of any size, as long as it retains its ability to direct a moiety associated with the targeting agent to the surface of a cell or to the surface of a particular type of cell.

As used herein, the term "therapeutic agent" means any agent having a therapeutic effect, including but not limited to chemotherapeutics, toxins, radiotherapeutics, or radiosensitizing agents. Also encompassed by the term are gene therapy vectors, antisense nucleic acid constructs and transcription factor decoys.

As used herein, the term "transcription factor" means a polypeptide that is involved in the transcription of DNA. Transcription factors can, but are not required to bind DNA. A transcription factor can function in response to an external stimulus, or a transcription factor's action can be constitutive.

As used herein, the terms "transcription factor decoy" and "decoy" are used interchangeably and mean molecules that bind to or interact with transcription factors and/or prevent their binding to native enhancer sequences. Decoys include nucleic acid sequences, including, but not limited to, oligonucleotides that correspond to (i.e., are identical to or essentially identical to) the native enhancer. Such oligonucleotides include, but are not limited to: single stranded palindromic oligonucleotides comprising one or more repeats of the enhancer sequence; sense and antisense oligonucleotides comprising one or more repeats of the enhancer sequence; oligonucleotides that form hairpin structures such that a duplex binding site for the transcription factor is generated; and one or more oligonucleotides that form a cruciform structure such that one or more binding sites for the transcription factor are generated; and double stranded DNA sequences that have a higher affinity for a genomic binding site of a transcription factor than does the natural DNA sequence.

As used herein, the term "wild-type" means the naturally occurring form of a protein or nucleic acid sequence. The term is not used to denote a baseline from which a mutation is established. The term "wild-type" is meant to describe the form of a protein or nucleic acid sequence as it is most commonly found in nature.

II. General Considerations

The present invention pertains in part to the regulation and modulation of gene expression. Gene expression can be regulated by placing a foreign DNA or RNA oligonucleotide (or an analog such as phosphorothionate DNA/RNA) in the cell for the purpose of (a) incorporation into the genome; (b) expression of a gene (which is sometimes considered "transient transfection"); (c) altering regulatory protein concentrations (wherein a vehicle can act as a transcription factor decoy); (d) altering RNA splicing; (e) binding to messenger RNA in the cytoplasm, (f) RNA interference or (g) altering the expression of a segment of DNA by inducing the formation of untranscribable structures, such as a triple helix. The strategy for (a), (b) and (g) generally involves the delivery of a relatively long double stranded DNA oligomer to the nucleus. The strategy for (c) through (g) can involve a short DNA oligomer that is an operator (i.e. sequence of DNA known to act as a binding site) for a particular regulatory protein.

The strategy for (d) and (e) can involve RNA, DNA or analogs such as peptide nucleic acids and morpholino DNA/RNA oligonucleotides as well as the use of antisense oligonucleotides. However, there has been a great deal of difficulty implementing antisense strategies. At the present time, it is thought that perhaps this is related to a delivery problem or, alternatively, that the cell has a mechanism for overcoming the reduction in concentration of a particular message. In either case, delivery of oligonucleotides to the nucleus is still a requirement for strategies (a) through (d).

For strategies (e) and (f), it might only be necessary to deliver an oligonucleotide to the cytoplasm, but this will depend on how the oligonucleotide is to be intercepted.

Consequently, the controlled delivery of oligonucleotides is a key to understanding the mechanism and effecting control of gene expression. The present invention directly addresses this historic antisense problem.

A goal of the present invention is the regulation and/or perturbation of gene expression. This is of use both for research purposes and also in therapeutic applications. Delivery is a major obstacle in the use of oligonucleotides and chemically modified oligonucleotides for these applications. Nanoparticles of various compositions can be used to achieve a desired result. Materials such as titanium, titanium dioxide, tin, tin oxide, silicon, silicon dioxide, iron, iron$^{III}$ oxide, silver, nickel, gold, copper, aluminum and other materials can be used, however gold is a preferred material. Gold nanoparticles possess several advantages. First, gold nanoparticles offer the ability to easily regulate nanoparticle size and, as explained below, subcellular localization. Additionally, synthesis of such nanoparticles is facile, and many art-recognized techniques are available.

Nanoparticles can be conveniently produced by known methods, including emulsion polymerization in a continuous aqueous phase, emulsion polymerization in continuous organic phase, interfacial polymerization, solvent deposition, solvent evaporation, dissolution of an organic polymer solution, cross-linking of water-soluble polymers in emulsion, dissolution of macromolecules, and carbohydrate cross-linking. These fabrication methods can be performed with a wide range of materials. Metal atoms, and structures comprising metal atoms, can also serve as effective nanoparticles. Nanoparticles can be solid or can comprise a hollow structure that can contain a material.

A delivery vehicle of the present invention can comprise one or more appropriate oligonucleotides associated with a nanoparticle. Next, a nuclear localization signal or other localization peptides that will help with transport and direct the nanoparticle to the nucleus are associated with the nanoparticle. The size of the nanoparticle can be used to prevent transport to the nucleus when this is desirable. Finally, appropriate proteins can also be localized on the surface of the particle. Appropriate proteins can comprise ligases, restriction enzymes or other DNA processing enzymes useful for a given application. The localization and effect of the delivery vehicle can then be identified using transmission electron microscopy, Raman microscopy, confocal microscopy and other analytical techniques for determining the concentration and localization of the active nanoparticles in the cell. Even delivery vehicles comprising nanoparticles as small as 5 nm can be identified using one or more of the above analytical techniques.

Thus, the present invention provides a novel approach to solving the problems of nanoparticles as drug delivery vehicles encountered in the art. Specifically, the present invention discloses nanoparticles that do not necessarily encapsulate a biologically active structure, but rather serve as a scaffold for the biologically active structure to be attached to the surface of the nanoparticle. Significantly, the nanoparticles of the present invention can also comprise a nuclear localization signal, which can target a therapeutic agent to the nucleus of a cell. Until the disclosure of the present invention, nuclear localization signals have not been used to direct a nanoparticle across both the plasma membrane and the nuclear membrane.

In another aspect of the present invention, a plurality of sequences can be associated with a nanoparticle delivery vehicle. Various sequences, such as RME sequences, can also be associated with a vehicle. These additional sequences can aid in the translocation of a vehicle across various membranes, such as the nuclear membrane of a cell or the outer membrane of a cell. Thus, if membranes and other structures that generally inhibit translocation of a vehicle to a given location in or on a cell are analogized as "locks", NLS and RME sequences can be analogized to be "keys". Thus, in a preferred embodiment, a nanoparticle delivery vehicle of the present invention can comprise a plurality of different sequences or "keys," which can enable a given nanoparticle delivery vehicle to pass through various potential barriers to translocation and can provide for the targeting of a variety of different cell types.

The present invention describes a nanoparticle delivery vehicle that can be used with a variety of subjects including warm blooded animals, particularly mammals, including humans, dogs, cats and other small animals, and farm animals. Additionally, the nanoparticles of the present invention can be used with prokaryotic and eukaryotic microorganisms and with in vitro cultures. The nanoparticle delivery vehicle of the present invention can be used as a diagnostic agent in all of the above subjects, as well as in the capacity of a therapeutic agent. There is no limitation on the type of biologically active structure the subject to which a nanoparticle of the present invention can be introduced. See, e.g., U.S. Pat. Nos. 5,783,263 and 6,106,798. See also, *Colloidal Drug Delivery Systems*, (1994) (Kreuter, ed.), Marcel Dekker, Inc., New York, pp 219-342; Kreuter, (1994) *Eur. J. Drug Metab. Ph.* 3: 253-56.

IV. Selection and Preparation of a Targetable Nanoparticle Delivery Vehicle

A targetable nanoparticle delivery vehicle of the present invention preferably comprises at least three components: a nanoparticle, one or more targeting agents (e.g. "keys" such as nuclear localization signals and cell surface targeting signals) and one or more active agents. The active agent can be one or more of any chemical entity, for example, a peptide sequence, a single stranded nucleic acid oligomer, a double stranded nucleic acid oligomer, a peptide nucleic acid or a small molecule. These three components are prepared and joined together to function as a delivery vehicle, which can be targeted a cell's nucleus via the nuclear localization signal. Active agents and nuclear localization signals can be synthesized using primers or templates previously associated with the nanoparticle. The nuclear localization signal directs the translocation of the delivery vehicle to the nucleus of a cell, whereupon the active agent can interact with one or more proteins or nucleic acids to facilitate a desired effect. If a nanoparticle of larger size is selected, for example greater than or equal to about 30 nm, the delivery vehicle will be translocated to a cell's cytoplasm.

A targetable nanoparticle delivery vehicle of the present invention can further comprise an extracellular targeting agent. In this embodiment, a nanoparticle delivery vehicle can comprise two targeting signals. First, a targeting agent can be selected which can direct a delivery vehicle to the surface of a target structure that recognizes the selected targeting agent. Second, a nuclear localization sequence can be included, which will direct a delivery vehicle to the nucleus of a target structure.

IV.A. Selection and Preparation of a Nanoparticle

There are no limits on the physical parameters of a nanoparticle component of the present invention, although the design of a delivery vehicle should take into account the biocompatibility of the nanoparticle vehicle, where appropriate. The physical parameters of a nanoparticle vehicle can be optimized, with the desired effect governing the choice of size, shape and material. Preferred particle sizes for transport to a cell's nucleus are on the order of 5 nm although, as discussed below, larger particles might be desired for a given application. Additionally, particles smaller than about 25 nm in diameter are preferred for use in nuclear targeting to facilitate entry into the nucleus via a nuclear pore. (Feldherr & Akin, (1990) *Electron Microsc. Rev.* 3(1):73-86; Feldherr et al., (1992) *Proc. Natl. Acad. Sci. U.S.A.* 89:11002-5; Feldherr & Akin, (1999) *J. Cell Sci.* 112:2043-48; Feldherr & Akin, (1994) *Exp. Cell Res.* 215:206-10.)

The nanoparticle, which can also be referred to as a scaffold, of a nanoparticle delivery vehicle can comprise a variety of inorganic materials including, but not limited to, metals, semi-conductor materials or ceramics. Preferred metal-based compounds for the manufacture of nanoparticles include titanium, titanium dioxide, tin, tin oxide, silicon, silicon dioxide, iron, iron$^{III}$ oxide, silver, gold, copper, nickel, aluminum, steel, cobalt-chrome alloys, cadmium (preferably cadmium selenide) and titanium alloys. Preferred ceramic materials include brushite, tricalcium phosphate, alumina, silica, and zirconia. The nanoparticle can be made from organic materials including carbon (diamond). Preferred polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also suitable for use as a nanoparticle scaffold. Gold is especially preferred due to its well-known reactivity profiles and biological inertness.

Nanoparticles comprising the above materials and having diameters less than 1,000 nanometers are available commercially or they can be produced from progressive nucleation in solution (e.g., by colloid reaction), or by various physical and chemical vapor deposition processes, such as sputter deposition. See, e.g., Hayashi, (1987) *Vac. Sci. Technol.* July/August 1987, A5(4):1375-84; Hayashi, (1987) *Physics Today*, December 1987, pp. 44-60; *MRS Bulletin*, January 1990, pgs. 16-47.

Alternatively, nanoparticles can be produced using HAuCl$_4$ and a citrate-reducing agent, using methods known in the art. See, e.g., Marinakos et al., (1999) *Adv. Mater.* 11: 34-37; Marinakos et al., (1998) *Chem. Mater.* 10: 1214-19; Enustun & Turkevich, (1963) *J. Am. Chem. Soc.* 85: 3317. Tin oxide nanoparticles having a dispersed (in H$_2$O) aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif. Biodegradable, ceramic and polymeric nanoparticle materials will be known to those of skill in the art and can comprise a biodegradable composition.

Besides sputter deposition, plasma-assisted chemical vapor deposition (PACVD) is another technique that can be used to prepare suitable nanoparticles. PACVD functions in relatively high atmospheric pressures (on the order of one torr and greater) and is useful for generating particles having diameters of about 1000 nanometers and smaller. For example, aluminum nitride particles having diameters of less than 1000 nanometer can be synthesized by PACVD using Al(CH$_3$)$_3$ and NH$_3$ as reactants. The PACVD system typically includes a horizontally mounted quartz tube with associated pumping and gas feed systems. A susceptor is located at the center of the quartz tube and heated using a 60 KHz radio frequency source. The synthesized aluminum nitride particles are collected on the walls of the quartz tube. Nitrogen gas is commonly used as the carrier of the Al(CH$_3$)$_3$. The ratio of Al(CH$_3$)$_3$:NH$_3$ in the reaction chamber is controlled by varying the flow rates of the N$_2$/Al (CH$_3$)$_3$ and NH$_3$ gas into the chamber. A constant pressure in the reaction chamber of 10 torr is generally maintained to provide deposition and formation of the ultrafine aluminum nitride nanoparticles. PACVD can be used to prepare a variety of other suitable biodegradable nanoparticles.

Figure 1B:
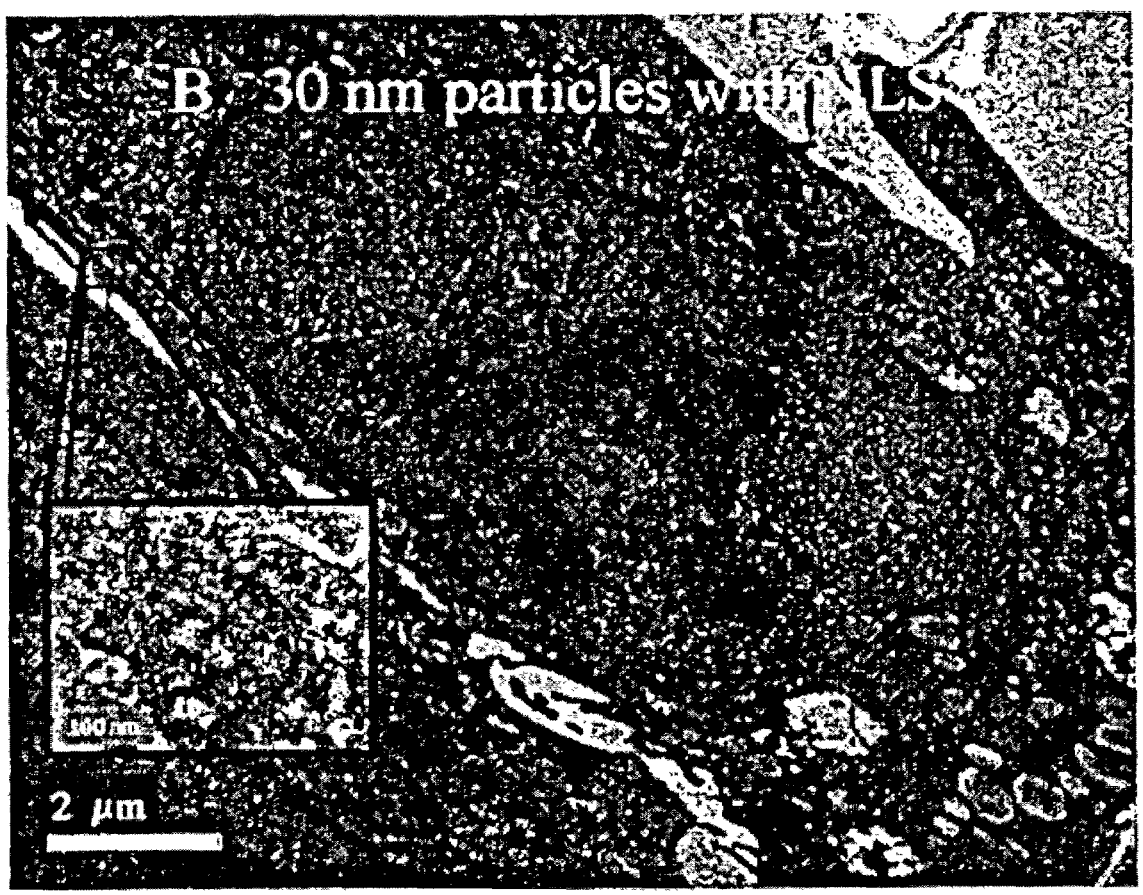
FIG. 1B is a transmission electron micrograph of hepatocytes grown in a medium comprising 30 nm nanoparticles. A region of the cytoplasm including a vacuole is highlighted in the inset.

The size of a nanoparticle can be an important consideration. Larger nanoparticles, on the order of greater than or equal to about 30 nm, are seen to enter cells, but are not translocated across the nuclear membrane into the nucleus of a cell, as seen in FIG. 1B. Presumably, this effect is directly related to the size of the nanoparticle, since 5 nm nanoparticles do cross the nuclear membrane and are translocated into the nucleus, as seen in FIG. 1A. Thus, selection of the appropriate delivery vehicle size will be important, but also offers an additional level of targetability and facilitates the design and employment of nanoparticles carrying active agents that need to be located in the cytoplasm and not the nucleus.

IV.B. Selection and Preparation of an Active Agent

Having selected and prepared a nanoparticle to which at least a nuclear localization signal and preferably another, different targeting agent are attached, a desired active agent is selected and prepared. Appropriate active agents can comprise any small molecule, protein or nucleic acid sequence, and the selection is governed by the intended application of the delivery vehicle. Various applications of nanoparticle delivery vehicles of the present invention are discussed in depth below, and include gene therapy, modulation of gene expression, altering RNA splicing and modulation of protein-protein interactions. Appropriate active agents will be apparent to one of skill in the art upon review of the present disclosure and will be selected with to regard to a desired experimental or clinical goal.

It is also an aspect of the present invention to provide a nanoparticle delivery vehicle comprising two or more different active agents, e.g. 2, 3, 4, 5, or other desired number of different active agents. Thus, delivery of the different active agents can be accomplished in the same cellular or tissue location, or in two or more different cellular or tissue locations, depending on the targeting sequences that are employed.

Any combination of any of the active agents disclosed herein can be provided. For example, a nanoparticle delivery vehicle comprising a therapeutic agent and an imaging agent can be provided, for use in for example, delivery to a tumor. As another example, a nanoparticle delivery vehicle comprising a chemotherapeutic agent and a radiosensitizing agent can be provided. As yet another example, a nanoparticle delivery vehicle comprising different polynucleotide sequences for use in modulation of transcription and/or translation of the same or different genes can be provided.

IV.B.1. Selection of an Active Agent

Generally, a single stranded nucleic acid sequence appropriate for use as an active agent in the present invention can be selected on the basis of the context in which the present invention is employed. In one embodiment, appropriate single stranded DNA are complementary to a nucleic acid sequence known or suspected to be present in a disease condition. In another embodiment, appropriate single stranded DNA is complementary to an overexpressed gene. Functional equivalents of known sequences can also be used as active agents and are considered to be an aspect of the present invention. Nucleic acid sequences of any manageable length can be used as an active agent. Typically, such agents range between about 20 and about 50 nucleotides in length, although longer sequences can be used. In yet another embodiment, a nucleic acid sequence corresponding to a full-length gene, or a fragment thereof, can be used as an active agent.

Double stranded DNA of various lengths and compositions is suitable for use as an active agent in the present invention. Double stranded DNA can be of any length, from a few base pairs up to the length of a full-length gene. As discussed below, long lengths of DNA, and notably full-length genes, find utility in gene therapy applications. In this embodiment, full-length genes can be incorporated into a host cell's genome, or can be transiently expressed within the cell. In this embodiment, then, a cell is lacking a particular gene and an appropriate double stranded DNA sequence selected as an active agent is the gene absent from the cell's genome.

Nucleic acid analogs can also be used as active agents in the present invention. In one aspect of the present invention, peptide nucleic acid analogs (PNAs) can be used as active agents. A peptide nucleic acid analog is a DNA analog wherein the backbone of the analog, normally a sugar backbone in DNA, is a pseudopeptide. A PNA backbone can comprise a sequence of repeated N-(2-amino-ethyl)-glycine units. Peptide nucleic acid analogs react as DNA would react in a given environment, and can additionally bind complementary nucleic acid sequences. Peptide nucleic acid analogs offer the potential advantage over unmodified DNA of the formation of stronger bonds, due to the neutrally charged peptide backbone of the analogs, and can impart a higher degree of specificity than is achievable by unmodified DNA.

PNAs have been employed in a wide array of biochemical roles, which is applicable to the present invention, including sequence mapping. In vitro studies indicate that PNA could inhibit both transcription and translation of genes to which it has been engineered with a complementary sequence. This suggests that PNAs could be useful in antigene and antisense therapy. See, e.g., Norden et al., (2000) *FASEB J.* 14(9): 1041-60. To date, however, researchers have been unable to reproducibly target such a sequence to the cell nucleus from outside the plasma membrane.

The present invention addresses this problem and offers potential for heretofore unattainable applications of PNAs. PNAs suitable for use as active agents in the present invention will, therefore, comprise a sequence complementary to a sequence of interest. Other nucleic acid analogs useful in the context of the present invention include morpholino nucleic acid analogs. Morpholino analogs can be substituted for a nucleic acid sequence and has the benefits of both complementarity and a unique chemical reaction and binding profile not found in native nucleic acid sequences. See, e.g., Chakhmakhcheva et al., (1999) *Nucleos. Nucleot.* 18: 1427-28.

Additionally, proteins are appropriate for use as an active agent in the present invention. In one embodiment, appropriate proteins comprise proteins known to interact with proteins associated with DNA replication and expression, for example, ligases. In this embodiment, a nanoparticle-bound protein can be a protein that interacts with DNA or RNA sequences, possibly as an up- or downregulator of the transcription process, the translation process or both. In an alternative embodiment, the present invention can be used to prove or disprove a putative protein-protein interaction. In this case, the nanoparticle-bound sequence is a probe protein and the application of the invention can give data similar to that achievable using the well-characterized yeast two-hybrid system and other analytical systems, although the present invention affords the opportunity to examine such an interaction in situ. More specifically, proteins capable of interacting with receptors on nuclear regulatory proteins can be employed as active agents.

Finally, small molecules attached to a nanoparticle can be used as active agents in the present invention. Appropriate small molecules will have the ability to interact with enzymes, cofactors, nucleic acids and other intracellular structures. Small molecules can be those identified as natural ligands, inhibitors (competitive, uncompetitive and noncompetitive) or designed modulators. Chemotherapeutic agents, radiotherapeutics, or radiosensitizing agents; an imaging agent; a diagnostic agent; or other agent known to interact with an intracellular protein, a nucleic acid or a soluble or insoluble ligand can also be used as active agents.

It should be noted that the use of one of the above active agents does not preclude the binding of a different active agent to the nanoparticle and several active agents can be joined to a single nanoparticle. Moreover, active agents can be multivalent and/or multifunctional.

IV.B.2. Preparation of an Active Agent

Nucleic acid sequences useful as active agents in the context of the present invention can be prepared in a variety of ways and will be apparent to one of skill in the art upon review of the present disclosure. For example, an appropriate DNA sequence can be excised from a larger DNA sample using restriction endonucleases, which sever nucleic acid sequences at known sequences. Excised nucleic acid sequences can be excised and purified using methods known in the art. See, e.g., Sambrook et al., (1992) *Molecular Cloning: A Laboratory Manual*, Cold Spring Harbor, N.Y. for a general discussion of cloning strategies. Alternatively, and more preferably, nucleic acid sequences can be synthesized using well-known manual and automated nucleic acid synthesis methods. All nucleic acid sequences that are used as active agents, whether they are excised, synthesized or otherwise prepared, should be substantially pure. Synthesis of nucleic acid or protein active agents can proceed using a template previously associated with a nanoparticle.

Isolation and purification of proteins will correspond with techniques established for preparation of a given protein; those proteins of interest that have not been purified can be isolated using methods known to those of skill in the art and are not discussed here. Similarly, strategies of synthesizing and purifying small molecules can be found in the art and will be evident to one of skill in the art of organic chemistry or other chemical discipline.

IV.C. Selection and Preparation of a Nuclear Localization Signal

The inclusion of a nuclear localization signal (NLS) as a delivery vehicle component is an aspect of the present invention. A representative nuclear localization signal is a peptide sequence that directs the protein to the nucleus of the cell in which the sequence is expressed. A nuclear localization signal is predominantly basic, can be positioned almost anywhere in a protein's amino acid sequence, generally comprises a short sequence of four amino acids (Autieri & Agrawal, (1998) *J. Biol. Chem.* 273: 14731-37) to eight amino acids, and is typically rich in lysine and arginine residues (Magin et al., (2000) *Virology* 274: 11-16). Nuclear localization signals often comprise proline residues. A variety of nuclear localization signals have been identified and have been used to effect transport of biological molecules from the cytoplasm to the nucleus of a cell. See, e.g., Tinland et al., (1992) *Proc. Natl. Acad. Sci. U.S.A.* 89:7442-46;

Moede et al., (1999) *FEBS Lett.* 461:229-34. Translocation is currently thought to involve nuclear pore proteins.

In a preferred embodiment of the present invention, a nuclear localization signal be attached to the nanoparticle. The nuclear localization signal can be synthesized or excised from a larger sequence. As noted, a variety of nuclear localization signals are known and selection of an appropriate sequence can be made based on the known properties of these various sequences. Representative NLS's include the monopartite sequence PKKKRKV (SEQ ID NO: 1) and the bipartite sequence KRPAAIKKAGQAKKKK (SEQ ID NO: 2).

Nuclear localization signals appear at various points in the amino acid sequences of proteins. NLS's have been identified at the N-terminus, the C-terminus and in the central region of proteins. Thus, a selected sequence can serve as the functional component of a longer peptide sequence. The residues of a longer sequence that do not function as component NLS residues should be selected so as not to interfere, for example tonically or sterically, with the nuclear localization signal itself. Therefore, although there are no strict limits on the composition of an NLS-comprising sequence, in practice, such a sequence can be functionally limited in length and composition.

In another aspect of the present invention, a plurality of sequences can be associated with a nanoparticle delivery vehicle. Various sequences, such as RME sequences, can also be associated with a vehicle. These additional sequences can aid in the translocation of a vehicle across various membranes, such as the nuclear membrane of a cell or the outer membrane of a cell. Thus, if membranes and other structures that generally inhibit translocation of a vehicle to a given location in or on a cell are analogized as "locks", NLS and RME sequences can be analogized to be "keys". Thus, in a preferred embodiment, a nanoparticle delivery vehicle of the present invention can comprise a plurality of different sequences or "keys," which can enable a given nanoparticle delivery vehicle to pass through various potential barriers to translocation.

IV.D. Selection and Preparation of a Cell Surface Receptor Recognition Moiety

In one aspect of the present invention, a moiety that imparts the ability to be recognized and/or bound by a cell surface receptor is bound to the nanoparticle. This moiety will generally comprise a protein sequence known to be recognized by a cell surface receptor. Preferably, the cell surface receptor recognition moiety can further comprise a nucleic acid sequence, either alone or as part of a nucleic acid-protein hybrid, or peptide analog. A vast number of cell surface receptors are known and can be useful in the present invention, including the macrophage mannose receptor and its various homologs, and those associated with retroviruses such as HIV.

A representative, but non-limiting, list of moieties that can be employed as targeting agents in the present invention is presented in Table 1. Homologs of the presented moieties can also be employed. These targeting agents can be associated with a nanoparticle and used to direct the nanoparticle to a target structure, where it can subsequently be internalized. There is no requirement that the entire moiety be used as a targeting agent. Smaller fragments of these moieties known to interact with a specific receptor or other structure can also be used as a targeting agent. The targeting agents of Table 1 can function to internalize (e.g., by receptor mediated endocytosis) a delivery agent interacting with a targeting agent.

TABLE 1

Diptheria Toxin
Pseudomonas toxin
Cholera toxin
Ricin
Concanavalin A
Rous sarcoma virus
Semliki forest virus
Vesicular stomatitis virus
Adenovirus
Transferrin
Low Density Lipoprotein
Transcobalamin
Yolk Proteins
IgE
Polymeric IgA
Maternal IgG
IgG, via Fc receptors
Insulin
Epidermal Growth Factor
Growth Hormone
Thyroid Stimulating Hormone
Nerve Growth Factor
Calcitonin
Glucagon
Prolactin
Luteinizing Hormone
Thyroid hormone
Platelet Derived Growth Factor
Interferon
Catecholamines
Nuclear Localization Signal The recognition moiety can further comprise a sequence that is subject to enzymatic or electrochemical cleavage. The recognition moiety can thus comprise a sequence that is susceptible to cleavage by enzymes present at various locations inside a cell, such as proteases or restriction endonucleases (e.g. DNAse or RNAse).

It must be emphasized that a cell surface recognition sequence is not an absolute requirement for the present invention. Indeed, as shown in FIG. 1A, hepatocytes grown in media containing nanoparticles lacking a cell surface recognition sequence were translocated across the cell membrane, in the absence of such a sequence. Thus, although a cell surface receptor sequence can be useful for targeting a given cell type, or for inducing the association of a nanoparticle with a cell surface, there is no requirement that a cell surface recognition sequence be present on the surface of a nanoparticle in order to practice the present invention.

The presence of a cell surface receptor unique to a given type of cell can assist in the selection and delivery of an active agent to that cell type. For example, macrophages express a cell surface receptor (the macrophage mannose receptor) that mediates pinocytosis of particles that comprise mannose through carbohydrate recognition domains. See, Mullin et al., (1997) *J. Biol. Chem.* 272: 5668-81. Thus, the selection of an appropriate cell surface receptor can facilitate cell specific selection by a nanoparticle delivery vehicle and consequently, cell specific interaction.

IV.E. Selection and Preparation of a Tether Sequence

In another aspect of the present invention, a short tether sequence can be disposed between the nanoparticle and a cell surface recognition sequence of a nanoparticle delivery vehicle of the present invention. The tether can be a protein sequence, a nucleic acid sequence or any other composition that is compatible with an intracellular environment. In the present invention, protein and nucleic acid sequences are preferred due to their enzymatic cleavability. For example, a nucleic acid tether that comprises a known cut site for a restriction endonuclease found in the targeted cell can be employed. Alternatively, a protein tether can be employed that comprises a cut site for a protease commonly found in the targeted cell type. Finally, a tether can be designed that can be chemically or electrochemically cleaved.

Cleavage of a tether is one method by which the nanoparticle, which will comprise an active agent and a nuclear localization signal, can be freed to translocate across the nuclear membrane and into the nucleus of a cell. In one example, upon association of a cell surface receptor with a cell surface recognition sequence disposed on the surface of a nanoparticle of a delivery vehicle of the present invention, the nanoparticle delivery vehicle is, in effect, bound to the cell surface. Upon translocation of the delivery vehicle to the interior of a cell, by endocytosis or other mechanism, the nanoparticle delivery vehicle remains bound to the receptor. In order to free the nanoparticle delivery vehicle and its associated active agent, the tether can be cleave by endogenous proteases, nucleases or other chemical or electrochemical techniques. Cleavage of the tether sequence frees the nanoparticle delivery vehicle and enables subsequent direction of the delivery vehicle to the nucleus, via the nuclear localization signal disposed on the nanoparticle surface.

IV.F. Assembly of a Nanoiarticle Delivery Vehicle

Having selected and prepared the various individual components of a nanoparticle delivery vehicle of the present invention, the agent itself is then assembled. The order of assembly is not critical and can be governed primarily by the requirements of a desired chemical reaction. The chemical properties of an active agent, an NLS, a nanoparticle, as well as physiological and various other considerations, should also be weighed. Thus, the assembly procedure described hereinbelow is presented in an arbitrary order. Further, the materials described, i.e. composition of the nanoparticle, etc., are presented only as examples and are not meant to be limiting in any way. Suitable materials and sequences will be known to those of skill in the art when evaluated in light of the present disclosure and the knowledge and resources available to researchers in the applicable fields.

IV.F.1. Association of an Active Agent with a Nanoparticle

Following selection and preparation of a nanoparticle and a suitable active agent, the two components are joined to form a complex. In one embodiment, the nanoparticle is fashioned of gold. Gold is particularly useful in the present invention due to its well-known reactivity profile and its relatively inertness in the context of biological systems. Colloidal gold can be used, although the overall negative charge of common preparations of gold imparts the quality that colloidal gold has a high non-specific affinity for certain proteins. The negative charge of a preparation can be imparted by association of gold molecules with negatively-charged ligands such as citrate or bis-sulfonatotriphenylphosphine. These negatively-charged ligands, and thus the overall negative charge associated with a colloidal gold preparation, are preferably reduced or eliminated by exchanging any negatively-charged ligands with neutral ligands, such as polyethylene glycol, or positively-charged ligands, such as amines.

Alternatively, the use of colloidal gold can be accompanied by additional treatments such that it can be coated at some point in the preparation process with another protein, such as BSA, in order to block undesired nonspecific protein binding. Small molecule and peptide coatings can also be used to avoid specific interactions with cellular proteins. For example, colloidal gold has been prepared with a coating of glutathione. Since glutathione, a natural antioxidant, is one of the most abundant peptides in the cell, this coating may impart to the nanoparticle a camouflage-like effect. Alternatively, some gold clusters and particles are commercially available and can be used in the present invention. For example, NANOGOLD® gold particles are available from Nanoprobes, Inc., Yaphank, N.Y. Also preferable for use in the present invention are biodegradable particles, which can be fashioned of an appropriate polymer or other material. Some commercially available nanoparticles are prepared for labeling prior to shipping and are convenient for attaching entities to the nanoparticles.

In one embodiment, using a gold nanoparticle as the nanoparticle and a single or double stranded nucleic acid as an active agent, a thiolation reaction can be performed to add a thiol group to the 5' end of the nucleic acid oligomer. Alternatively, an amination reaction can be performed and will proceed mutatis mutandis to the thiolation reaction described herein. The general purpose of the reaction is to introduce a nucleophilic center, which can subsequently be functionalized with a desired moiety. A representative thiol modifier phosphoramidite reagent is presented as Compound 1, which is available from Glen Research, Inc. of Sterling, Va.

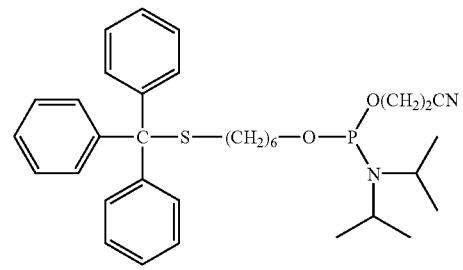

Compound 1

Nucleic acid oligmers are incubated with a thiol modifier phosphoramidite under conditions that permit attachment of the phosphine to the 5' end of the probe DNA. The reaction can be carried out in a DNA synthesizer using standard conditions. Compound 1 can be added as a step in automated DNA synthesis using an automated apparatus, such as the ABI® 3900 high-throughput DNA synthesizer (Applied Biosystems, Foster City, Calif.). The thiol modifier is added in the last step of synthesis of an oligonucleotide. The phosphine is oxidized using iodine and the purification is exactly the same as that used for unlabeled oligonucleotides. The purification process is easier for labeled oligonucleotides since labeled oligonucleotides are significantly more hydrophobic and therefore tend to elute much more slowly under typical HPLC conditions. The phosphoramidite reacts spontaneously with the 5' hydroxyl of DNA, which can be disposed in acetonitrile. In this reaction, the thiol group is protected by a protecting trityl or acetic thioester group and is separated from the 5'-phosphodiester by a variable length carbon linker. A six-carbon linker is present in Compound 1.

The nucleic acid complex is then subjected to thiol deprotection to remove the trityl group. Specifically, the protecting trityl group is removed by treatment with silver nitrate and dithiothreitol (DTT). The nucleic acid complex is incubated with a nanoparticle metal component. The two entities are joined at the thiol exposed by the removal of the trityl group during the deprotection reaction. The formed active agent-nanoparticle complexes (in this embodiment nucleic acid-nanoparticle complexes) can be maintained in the reaction vessel until use.

IV.F.2. Association of a Nuclear Localization Signal with a Nanoparticle

A suitable nuclear localization signal is joined to the active agent-nanoparticle complex. Nuclear localization signals can be synthesized using standard peptide chemistry techniques, or can be isolated by proteolytic cleavage from a larger protein. Isolated or synthesized nuclear localization signals can be of any size, with the only requirement that the sequence comprise at least a known NLS, which are typically four to eight amino acids in length. Protein and peptide purification methods suitable for preparing nuclear localization signals, which are isolated from larger proteins, are known in the art. See generally, *Protein Purification Applications: A Practical Approach*, (1989) (Harris & Angal, eds.) IRL Press; *Protein Purification: Principles, High Resolution Methods, Applications*, (1989) (Janson & Ryden, eds.) VCH Publishers.

The present invention also encompasses the preparation of and association of a protein-peptide conjugate with a nanoparticle. Such a conjugate can comprise, for example, a comparatively large protein and a comparatively small NLS. Although both entities comprise amino acids, the distinction of protein and peptide is made based on, among other criteria, the functionality of each entity. In a specific example, a protein-peptide conjugate can comprise BSA and an NLS. Protein-peptide conjugates can subsequently be bound to gold nanoparticles.

The chemistry of attaching proteins and peptides to gold nanoparticles is similar to the chemistry required for attaching nucleic acids to gold nanoparticles. In one aspect, a thiol reaction is performed. The reaction can involve a thiol group disposed on the nuclear localization signal, which can take the form of a terminal cysteine or methionine residue, or on the nanoparticle. The thiol group can be convenient reacted with a primary amine on the alternate entity. The primary amine can conveniently take the form of a terminal lysine or arginine residue in the nuclear localization signal, but can also be disposed on the surface of the nanoparticle. See, e.g., Hainfeld & Furuva, (1992) *J. Histochem. Cytochem.* 40: 177-84; Hainfeld, (1992) *Ultramicroscopy* 46: 135-44.

IV.F.3. Association of a Cell Surface Recognition Sequence with a Nanoparticle

An appropriate cell surface recognition sequence can be selected (for example, one selected from or based on those presented in Table 1) and prepared as described above in Section IV.D above. The sequence can be, essentially, a protein or a peptide known to bind to a receptor expressed on the surface of a given cell type. Thus, the same chemical reactions can be performed to associate a cell surface recognition sequence with a nanoparticle as are performed to associate a nuclear localization signal or a protein active agent with a nanoparticle. Continuing with the example from Section IV.F.2 above, a thiol-amine reaction can be performed to associate a thiol disposed on either the nanoparticle or the cell surface recognition sequence with a primary amine disposed on the alternate member of a thiol-amine reaction pair. Depending on the reactivity profiles and the order in which the various component parts of a nanoparticle delivery vehicle are bound to a nanoparticle, a scheme of site blocking can be developed. Such a scheme can prevent binding of an entity to undesired sites on the nanoparticle or on the component parts themselves.

IV.F.4. Association of a Tether Sequence with a Nanoparticle

A tether sequence can also be bound to a nanoparticle. Such a sequence can be disposed between the nanoparticle and a cell surface recognition sequence or other entity associated with the nanoparticle. In order to serve its purpose, the tether sequence preferably comprises a site at which chemical, electrochemical or enzymatic cleavage can take place. When a tether sequence comprises a single or double stranded nucleic acid sequence, the sequence can comprise a cut site for a nuclease known to be present in the cells to which the delivery vehicle is being introduced. When the tether is a protein, it can comprise a proteolytic site. Finally, when it is desired that the tether be cleaved photolytically, it can comprise a material amenable to photocleavage. Commercially available photocleavable tether sequences include various spacer phosphoramidites, available from Glen Research of Sterling, Va.

IV.F.5. Biocompatibility and Protection of the Delivery Vehicle

If the nanoparticle comprises a metal component such as gold, it is desirable to assure biocompatibility between the nanoparticle and a subject to which the delivery vehicle is being administered. Gold is relatively inert and less physiologically intrusive than other metals, but the detrimental effects of any metal or polymer nanoparticle material can be minimized by coating or otherwise wholly or partly covering the nanoparticle with a biocompatible substance. Compounds that can be used to achieve biocompatibility include polymers (such as polyethylene glycol-PEG), proteins (such as BSA), lipids (including membrane envelopes) and carbohydrates. Addition of these biocompatibility compounds can be performed following the addition of the other delivery vehicle components and can serve as the final synthetic step before introduction of the delivery vehicle to a subject or system.

These materials can also protective or masking agents for the delivery vehicle and the active agent(s) and targeting agent(s) attached thereto to prevent recognition by the immune system or other biological systems (e.g. proteases, nucleases (e.g. DNAse or RNAse), or other enzymes or biological entities associated with undesired degradation). Thus, the protective coating or shell provides cloaking or stealth features to facilitate that the delivery vehicle reaches a desired cell or tissue with the active agent(s) and targeting agent(s) intact.

IV.F.6. Associating Multiple Sequences with a Delivery Vehicle

Multiple sequences can be associated with a delivery vehicle of the present invention. By associating multiple sequences with a single vehicle, the vehicle can be adapted to pass through various cellular barriers, such as the cell membrane or a nuclear membrane. For example, a nanoparticle vehicle can comprise an NLS and a RME sequence. The RME sequence can assist in the translocation of a vehicle across the membrane of a cell. Once inside a cell, the NLS can target the vehicle to the nucleus of the cell.

Preferably any sequences associated with a nanoparticle delivery vehicle are independently associated with the vehicle, rather than forming components of a single long sequence. As indicated by the results disclosed in Laboratory Example 1, independent association of multiple sequences (preferably multiple different sequences) is a more efficient method targeting a nanoparticle delivery vehicle to a desired cellular structure. However, sequential association of multiple sequences can also be an effective method of directing a nanoparticle delivery vehicle to a given site, and this approach forms another aspect of the present invention.

V. Introduction of a Nanoparticle Delivery Vehicle to a Subject or Sample

After a sufficiently pure nanoparticle delivery vehicle (preferably comprising a nanoparticle, an active agent and an NLS) has been prepared, it might be desirable to prepare the vehicle in a pharmaceutical composition that can be administered to a subject or sample. Preferred administration techniques include parenteral administration, intravenous administration and infusion directly into any desired target tissue, including but not limited to a solid tumor or other neoplastic tissue. This can be achieved by employing a final purification step, which disposes the vehicle in a medium comprising a suitable pharmaceutical composition.

Suitable pharmaceutical compositions in accordance with the invention generally comprise an amount of the desired delivery vehicle-active agent in accordance with the dosage information (which is determined on a case-by-case basis), admixed with an acceptable pharmaceutical diluent or excipient, such as a sterile aqueous solution, to give an appropriate final concentration in accordance with the dosage information set forth above with respect to the active agent. Such formulations will typically include buffers such as phosphate buffered saline (PBS), or additional additives such as pharmaceutical excipients, stabilizing agents such as BSA or HSA, or salts such as sodium chloride.

For parenteral administration it is generally desirable to further render such compositions pharmaceutically acceptable by insuring their sterility, non-immunogenicity and non-pyrogenicity. Such techniques are generally well known in the art as exemplified by *Remington's Pharmaceutical Sciences*, (1980) (Osol, ed.) 16th Ed., Mack Publishing Company, Easton, Pa., incorporated herein by reference. Moreover, for human administration, preparations should meet sterility, pyrogenicity, general safety and purity standards as required by FDA Office of Biological Standards.

When delivery vehicles are being introduced into cells suspended in a cell culture, it is sufficient to incubate the cells together with the nanoparticle delivery vehicles an appropriate growth media, for example Luria broth (LB) or a suitable cell culture medium. Although other introduction methods are possible, these introduction treatments are preferable and can be performed without regard for the entities present on the surface of a delivery vehicle.

When in vitro experiments are to be performed, delivery vehicles can be added to directly to a selected cell growth medium before cells are introduced into the medium. Such a medium must, obviously, be compatible not only with the physiological requirements of the cells, but also with the chemical and reactivity profile of the delivery vehicle. The delivery vehicle's profile will be apparent to one of skill in the art upon review of the present disclosure and in view of the moieties bound to the nanoparticle.

V.A. Receptor Mediated Endocytosis of a Delivery Vehicle

Recognition and binding of a cell surface recognition sequence disposed on a nanoparticle delivery vehicle of the present invention is an aspect of the present invention. The present invention takes advantage of the understanding that a cell surface binding event is often the initiating step in a cellular cascade leading to a range of events, notably receptor-mediated endocytosis.

The above methods describe methods by which a delivery vehicle can be introduced into a sample or subject. These agents are translocated across the cell membrane in a variety of ways. However, when a cell recognition sequence is bound to a nanoparticle, a different type of internalization can occur, namely receptor mediated endocytosis.

The term "receptor mediated endocytosis" ("RME") generally describes a mechanism by which, catalyzed by the binding of a ligand to a receptor disposed on the surface of a cell, a receptor-bound ligand is internalized within a cell. Many proteins and other structures enter cells via receptor mediated endocytosis, including insulin, epidermal growth factor, growth hormone, thyroid stimulating hormone, nerve growth factor, calcitonin, glucagon and many others, including those presented in Table 1. In the context of the present invention, receptor mediated endocytosis affords a convenient mechanism for transporting a nanoparticle to the interior of a cell.

In RME, the binding of a ligand by a receptor disposed on the surface of a cell can initiate an intracellular signal, which can include an endocytosis response. Thus, an agent that is bound on the surface of a cell is invaginated and internalized within the cell. Subsequently, any tether sequence present on the nanoparticle can be cleaved by the cell's endogenous enzymes, thereby freeing the agent to deliver its active agent to the appropriate structure.

It must be reemphasized that RME is not the exclusive method by which a delivery vehicle can be translocated into a cell. Other methods of uptake that can be exploited by attaching the appropriate entity to a nanoparticle include the advantageous use of membrane pores. Phagocytotic and pinocytotic mechanisms also offer advantageous mechanisms by which a nanoparticle delivery vehicle can be internalized.

VI. Detection of a Nanoparticle Delivery Vehicle

Nanoparticle delivery vehicles of the present invention can be detected on both the interior and exterior of cells in a variety of ways. Indeed, the ability to select one of several techniques for detection is an aspect of the present invention. One method of detecting the presence of a nanoparticle delivery vehicle is by monitoring a sample for the homeostatic change the nanoparticle delivery vehicle is designed to produce. For some applications, however, it might be desirable to monitor the presence of a nanoparticle delivery vehicle by a different approach. Several, but not all, methods of detecting the presence of nanoparticle delivery agents can include the use of transmission electron, fluorescence and other microscopy techniques; spectroscopic-based detection; and detection methods involving proteins, such as immunological methods. Other methods are possible and will depend on the specific circumstances of the experiment or treatment protocol.

VI.A. Transmission Electron Microscopy Detection of a Nanoparticle Delivery Vehicle Transmission electron microscopy (TEM) can be used to determine the presence of a nanoparticle delivery vehicle. Nanoparticle delivery vehicles comprising nanoparticles of 5 nm and larger can be clearly visualized by TEM, as evidenced by the TEM images presented in FIGS. 1A and 1B. FIG. 1A depicts nanoparticle delivery vehicles comprising 5 nm nanoparticles. FIG. 1B depicts nanoparticle delivery vehicles comprising 30 nm nanoparticles. In both figures, the nanoparticle delivery vehicles comprise a nuclear localization signal. FIGS. 1A and 1B indicate that TEM is a useful method of detecting the presence and subcellular localization of nanoparticle delivery vehicles. Nanoparticle delivery vehicles comprising nanoparticles as small as 5 nm in size are visible, as depicted in FIG. 1A.

FIGS. 1A and 1B demonstrate that TEM can be used to detect the presence of a nanoparticle delivery vehicle in the nucleus of a cell. Nanoparticle delivery vehicles comprising 5 nm nanoparticles locate to the cell nucleus, as shown in FIG. 1A. Nanoparticle delivery vehicles comprising 30 nm nanoparticles remain in the cell's cytoplasm, as shown in FIG. 1B. Thus, TEM facilitates the detection of nanoparticle delivery vehicles and the subcellular localization of the delivery vehicles.

TEM can also be used to estimate the density of nanoparticle delivery vehicles in a region. A density calculation can be performed by counting the number of observed particles in a given area scanned by TEM. An understanding of the density of nanoparticle delivery vehicles in a defined region, such as a cell's nucleus or cytoplasm, can provide information regarding the size requirements for a nanoparticle, the effectiveness of a given nuclear localization signal and other parameters.

VI.B. Spectroscopic Detection of a Nanoparticle Delivery Vehicle

Nanoparticle delivery vehicles of the present invention can also be detected spectroscopically. UV, visible and IR spectroscopic methods can be employed in the present invention. The choice of detection method will typically depend on the experimental design. In one embodiment, nanoparticle delivery vehicles of the present invention can be indirectly detected using fluorescence spectroscopy.

Expression of GFP and other fluorescent marker proteins provided by an active agent of a nanoparticle delivery vehicle of the present invention can be detected by fluorescence and can act as an indicator of the presence of a nanoparticle delivery vehicle. Alternatively, a fluorescent moiety can be associated with the nanoparticle component of a nanoparticle delivery vehicle and in this way, the presence of the nanoparticle delivery vehicle itself can be identified.

VI.C. Microscopy-Based Detection of a Nanoparticle Delivery Vehicle

As noted in section VI.A above, TEM is one form of microscopy useful for detecting delivery vehicles. Other forms of microscopy, however, can also be employed. Microscopy techniques such as bright field microscopy, phase contrast microscopy, confocal microscopy and other techniques can be employed to detect the presence of delivery vehicles.

Phase contrast microscopy is typically used for the visualization of cellular organelles, and can be employed to detect the presence of delivery vehicles. Confocal microscopy can also be useful for detecting delivery vehicles. The resolution of any of the above microscopy techniques can be enhanced by the introduction of various contrast enhancement or other agents known to refine images and increase resolution.

VI.D. Protein-Based Detection of a Nanoparticle Delivery Vehicle

Protein-based detection of a nanoparticle delivery vehicle is also possible. For example, a second protein known to associate with a first protein bound to a nanoparticle can be labeled and used as a probe. Suitable labels include fluorescent moieties and other labels. Upon association of the first and second proteins, and therefore association of the labeled second protein and the nanoparticle delivery vehicle, the presence of the nanoparticle delivery vehicle is detectable by detecting the presence of the probe. Any suitable protein pair can be used to detect a nanoparticle delivery vehicle of the present invention; preferably, a first protein is associated with a nanoparticle and a second protein is labeled with a detectable label, and the two proteins are known to associate.

VII. Applications of the Nanoparticle Delivery Vehicles of the Present Invention The nanoparticle delivery vehicles of the present invention can be employed to deliver a variety of active agents to a variety of different cellular and subcellular locations. As described more fully below, the present invention is useful for analysis of gene expression; incorporating a nucleic acid sequence or a sequence comprising nucleic acid analogs into a cell's genome; altering the concentration of a regulatory protein in a cell; altering an RNA splicing pattern; and interacting with mRNA in the cytoplasm of a cell.

As a general rule, when nucleic acid sequences are being selected and manipulated, care should be taken wherever possible to minimize the potential for the formation of self-annealed structures. Sequences of any chemical composition that are predicted to give rise to self-annealing structures should be avoided when practicing the present invention.

Additionally, the stringency of hybridization conditions can be varied, with the general rule that the temperature should remain within approximately 10° C. of the duplex's predicted $T_m$, which is the temperature (under defined ionic strength and pH) at which 50% of the target sequence hybridizes to a perfectly matched probe. An example of stringent hybridization conditions for analysis of complementary nucleic acids having more than about 100 complementary residues is overnight incubation in 50% formamide with 1 mg of heparin at 42° C. A high stringency wash can be preceded by a low stringency wash to remove background probe signal. An example of medium stringency wash conditions for a duplex of more than about 100 nucleotides is incubation for 15 minutes in 1×SSC at 45° C. An example of low stringency wash for a duplex of more than about 100 nucleotides is incubation for 15 minutes in 4-6×SSC at 40° C. For short probes (e.g., about 10 to 50 nucleotides), stringent conditions typically involve incubation in salt concentrations of less than about 1.0 M sodium ion, typically about 0.01 to 1.0 M sodium ion (or other ion) concentration, at pH 7.0-8.3, at a temperature of at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

VII.A. Modulation and Analysis of Gene Expression

The nanoparticle delivery vehicles of the present invention can be used to modulate and analyze gene expression in a model system. It is fundamental that the expression of a gene of interest correlates with the production of mRNA transcribed from the gene's DNA sequence. Transcribed mRNA is subject to standard Watson-Crick base pairing rules. Thus, in one embodiment a nanoparticle delivery vehicle can be used to directly modulate expression of a gene by selecting an active agent that will remove any expression-inhibiting structures or will introduce expression-enhancing structures. In another embodiment, a delivery vehicle of the present invention is employed to mimic a component part of a cell's natural second messenger system and thereby modulate the transcription and translation of a given gene.

In one embodiment, a transcription factor or other protein having the ability to modulate protein expression, which has been presented to the cytoplasm or nucleus of a cell by a nanoparticle delivery vehicle of the present invention, modulates gene expression. Modulation encompasses both up- and downregulation of a gene. In this embodiment, a nanoparticle delivery vehicle comprises either a competent transcription or translation modulator (e.g., a transcription factor) or a nucleic acid sequence encoding a transcription or translation modulator in the role of active agent. Competent modulators can be active in the form in which they are bound to a nanoparticle, or they can be in a form that is activated by proteolytic or other enzymatic or chemical treatment in the cytoplasm or nucleus of a target cell. Similarly, nucleic acid sequences encoding a transcription or translation modulator can be translated by the translation machinery of the target cell, which can be used in a method analogous to a feedback inhibition loop: the target cell's expression machinery can be used to express the nucleic acid introduced by a delivery vehicle, which will then produce a protein can inhibit further protein expression.

In another embodiment, gene expression is modulated in a cell having protein whose expression is dependent on a given splicing pattern. In this embodiment, a nanoparticle delivery vehicle of the present invention comprising a morpholino oligonucleotide, PNA or other modified oligonucleotide of appropriate sequence that alters splicing, is introduced to target cells that comprise a gene whose expression is dependent on a splicing event. When a gene encoding green fluorescent protein ("GFP") is employed to detectably demonstrate this embodiment of the invention, in the absence of such a morpholino oligonucleotide, there is no GFP expression. In cells where the morpholino oligonucleotide delivered by a delivery vehicle of the present invention is present, alternate splicing events occur and the GFP gene is expressed and can be detected spectrophotometrically. This example can be extended to any gene that can be spliced to generate a functional protein, with an appropriate nucleotide serving as an active agent bound on a delivery vehicle.

VII.B. Modulating Translation of a Protein

A delivery vehicle of the present invention can be used to deliver a nucleic acid sequence for incorporation into the genome of a target cell. This concept is sometimes referred to as "antisense" or "gene therapy". Breakthroughs in molecular biology and the Human Genome Project have opened previously unforeseen possibilities for targeted intervention with gene expression. These include permanent approaches such as transgenic overexpression or recombinant disruption of specific genes, as well as novel approaches for transient suppression of gene function. Short synthetic antisense (AS) oligodeoxynucleotides (ODN) designed to hybridize with specific sequences within a targeted mRNA belong to the latter class. Integration of a lacking gene into a host's genome has also been of significant interest.

AS intervention in the expression of specific genes can be achieved by the use of synthetic antisense oligodeoxynucleotides (AS-ODNs). See generally, Agrawal, (1996) *Trends Biotechnol.* 14(10): 376-87; Lev-Lehman et al., (1997) in *Antisense Therapeutics*, (Cohen & Smisek, eds.), Plenum Press, New York; and Lefebvre-D'Hellencourt et al., (1995) *Eur. Cytokine Netw.*, 6: 7-19; *Oligonucleotide & Gene Therapy—Base Antisense Therapeutics*, (1997), (Mori, ed.), Drug & Market Development Publications, Westborough, Mass.; *Antisense Therapeutics*, (1996) (Agrawal, ed.), Humana Press, Totowa, N.J. for general antisense reviews. AS-ODNs are short sequences of DNA, typically 15 to 25 bases in length, and are designed to complement a target mRNA of interest and to form an RNA:ODN duplex. This duplex formation can prevent processing, splicing, transport or translation of the relevant mRNA. Moreover, certain AS-ODNs can elicit cellular RNase H activity when hybridized with their target mRNA, resulting in mRNA degradation. Calabretta et al., (1996) *Semin. Oncol.*, 23: 78-87. In that case, RNase H will cleave the RNA component of the duplex and can potentially release the AS-ODN to further hybridize with additional molecules of the target RNA. An additional mode of action results from the interaction of AS-ODNs with genomic DNA to form a triple helix that might be transcriptionally inactive.

The nanoparticle delivery vehicles of the present invention can be used to vary a target cell's expression profile using the above discussion as a general guide. In one embodiment, a nanoparticle delivery vehicle can be prepared that comprises at least one AS sequence, an ODN sequence, an AS-ODN sequence or other nucleic acid or modified nucleic acid sequence. This sequence can serve as an active agent in a nanoparticle delivery vehicle. The nanoparticle delivery vehicle also comprises a nuclear localization signal, which targets the delivery vehicle to the nucleus of a cell. Alternatively, if it is desired that the nanoparticle delivery vehicle remain in the cytoplasm, nanoparticles of larger size (e.g., 30 nm) can be employed. The precise sequence and/or composition of an active agent reflects the role or roles of the nanoparticle delivery vehicle. For example, an active agent can be complementary to a gene of interest.

In practice, a nanoparticle delivery vehicle designed to vary a target cell's protein translation profile can be administered to a subject by injection or, if the target cells are present in an in vitro environment, the nanoparticle delivery vehicle can be added directly to the cell's growth medium. Both introduction procedures are described herein above, and others will be apparent to one of skill in the art upon review of the present disclosure.

VII.C. Modulating Regulatory Protein Concentration

The nanoparticle delivery vehicles of the present invention can be used to modulated the concentration of various cellular regulatory proteins. A specific example of regulation is known as using a transcription factor decoy. As stated herein above, the terms "decoy" and "transcription factor decoy" refer to molecules that bind to or interact with transcription factors and prevent their binding to native enhancer sequences. It is possible to design transcription factor decoys that specifically interact with transcription factors and mimic or resemble the natural genomic binding site for the particular transcription factor. Some transcription factor decoys can bind the transcription factor with an affinity near or exceeding its affinity for the natural genomic binding site.

Some transcription factors, in addition to binding an endogenous genomic binding site, can also bind to intracellular soluble ligands. Binding of such a transcription factor to an appropriate ligand subsequently alters the binding profile of the transcription factor to its genomic binding site or sites. Restated, ligand binding by a transcription factor can modulate the ability of the transcription factor to bind its intended genomic site. Such transcription factors are referred to in the art as intracellular or nuclear receptors for soluble ligands.

Transcription factor decoys can function in a variety of ways and thus can comprise a variety of elements. For example, nucleic acid sequences can compete with cellular target DNA for binding to one or more transcription factors. In this example, nucleic acid sequences can form a duplex with a target sequence and effectively inactivate the sequence. Nucleic acid sequences can be introduced that will form other duplex-type structures such as hairpins, cruciforms or other structures that will effectively inactivate cellular target DNA.

There is no requirement that a sequence introduced to cellular target DNA necessarily comprise unmodified nucleic acids. Sequences can comprise nucleic acid molecules that contain modified phosphodiester bonds. Modified phosphodiester bonds can include phosphorothioate, phosphoramidite, and methyl phosphate derivatives, for example.

The nanoparticle delivery vehicles of the present invention are able to facilitate a modulation in regulatory protein concentration. Modulation can be achieved by associating an appropriate active agent with a nanoparticle. For example, a short sequence of double stranded DNA, for which a given regulatory protein (e.g., transcription factor) has a high affinity, can be used as a transcription factor decoy, as described herein above. Additional regulatory protein-modulating applications for a delivery vehicle of the present invention will be apparent to one of skill in the art when considered in view of the present disclosure.

VII.D. Modulating RNA Splicing

Generally, the expression of a specific gene can be regulated at any step in the process of producing an active protein. Modulation of total protein activity can occur via transcriptional, transcript-processing, translational or post-translational mechanisms. One role of a nanoparticle delivery vehicle of the present invention is to modulate transcription of a nucleic acid sequence.

Transcription means a cellular process involving the interaction of an RNA polymerase with a gene that directs the expression as RNA of the structural information present in the coding sequences of the gene. The process includes, but is not limited to the following steps: (1) transcription initiation, (2) transcript elongation, (3) transcript splicing, (4) transcript capping, (5) transcript termination, (6) transcript polyadenylation, (7) nuclear export of the transcript, (8) transcript editing, and (9) stabilizing the transcript. Transcription can be modulated by altering the rate of transcriptional initiation or the progression of RNA polymerase (Maniatis et al., (1987) *Science*, 236: 1237-45). Transcript-processing can be influenced by circumstances such as the pattern of RNA splicing (the splicing of the RNA to yield one or more mRNA species), the rate of mRNA transport to the cytoplasm or mRNA stability.

Additionally, although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, can be target regions for an active agent of the present invention, and can be particularly useful in situations where aberrant splicing is implicated in disease, or where an overproduction of a particular mRNA splice product is implicated in disease. Aberrant fusion junctions due to rearrangements or deletions can also be targets.

The present invention can be employed to modulate RNA splicing. This aspect of the present invention can be accomplished by selecting an appropriate active agent, such as a nucleic acid sequence known to alter the splicing pattern for a given gene. The use of an appropriate sequence (e.g., DNA, RNA, morpholino nucleotide, etc.) can influence the splicing pattern and consequently the protein expression profile for a cell. Delivery of the appropriate sequence is the major obstacle in therapeutic applications of RNA splicing that can be overcome by employing nanoparticle delivery vehicles comprising a nuclear targeting capability.

VII.E. Interaction with mRNA in the Cytoplasm

The present invention can be used to interact with mRNA transcript for a given protein while the transcript is in the cytoplasm. Interaction can take a variety of forms, including modulation of the amount of a given protein produced by a cell. In one aspect of the present invention, a nanoparticle delivery vehicle of the present invention can employ an antisense nucleotide to interact with mRNA which has been exported to the cytoplasm. See, e.g., Bassell et al., (1999) *FASEB J.* 13: 447-54.

A nanoparticle delivery vehicle of the present invention can be designed to interact with mRNA in the cytoplasm of a cell. The specific hybridization of an oligomeric compound with mRNA can interfere with the normal function of the mRNA. This modulation of function of a nucleic acid by compounds that specifically hybridize to it is generally referred to as "antisense" and is discussed herein above. Antisense compounds can interrupt various functions of RNA can include all vital functions such as, for example, translocation of the RNA to the site of protein translation, translation of protein from the RNA, splicing of the RNA to yield one or more mRNA species, and catalytic activity which might be engaged in or facilitated by the RNA. The overall effect of such interference with mRNA function is the modulation of the expression of the protein for which the mRNA codes.

Association of an antisense compound with, for example, mRNA, can be utilized for diagnostics, therapeutics, prophylaxis and as research reagents and kits. When used as a therapeutic, a subject suspected of having a disease or disorder that can be treated by modulating the expression of a given protein can be treated by administering a nanoparticle delivery vehicle of the present invention comprising an antisense active agent. Use of the nanoparticle delivery vehicles of the present invention, when antisense compounds are included as the active agent, can also be used prophylactically, e.g., to prevent or delay infection, inflammation or tumor formation, for example.

Antisense-bearing delivery vehicles of the present invention are useful for research and diagnostics, because the antisense component can hybridize with nucleic acids encoding a particular protein of interest, enabling sandwich and other assays to easily be constructed to exploit this fact.

Additionally, the nanoparticle delivery vehicles of the present invention can be localized subcellularly through the selection of an appropriately sized nanoparticle. As shown in FIG. 1B, delivery vehicles comprising nanoparticles of 30 nm or greater remain localized to the cytoplasm of a cell and are not localized in the cell's nucleus, regardless of the presence or absence of a nuclear localization signal. This observation indicates that larger nanoparticles can be targeted to the cytoplasm, wherein untranslated mRNA is localized. Smaller nanoparticles can be used to target pre-mRNA in the nucleus. Thus, a delivery vehicle of the present invention can be targeted to the cytoplasm of a cell, where it can interact with RNA sequences disposed therein.

VIII. Advantages of the Delivery Vehicles of the Present Invention

There are a number of advantages of the present invention over the methods for delivery presently known in the art. First, there is a distinct advantage in the use of a nuclear localization signal. The inclusion of an NLS as a component part of a nanoparticle delivery vehicle assures that, assuming optimization of other variables, the nanoparticle delivery vehicle is targeted directly to the nucleus of a cell. This advantage greatly increases the efficacy of an active agent designed to interact with nuclear structures by increasing the amount of material delivered to the nucleus of a target cell; inclusion of the NLS results in less material disposed in the cytoplasm for shorter periods of time and ultimately less degradation of material. The NLS additionally offers the ability to effectively target cellular processes that occur in the nucleus, such as DNA replication, transcription, and various splicing events.

The association of additional targeting agents can aid in the translocation of a vehicle across various membranes, such as the nuclear membrane of a cell or the outer membrane of a cell, thus providing another advantage. If membranes and other structures that generally inhibit translocation of a vehicle to a given location in or on a cell are analogized as "locks", NLS and RME sequences can be analogized to be "keys". Thus, in a preferred embodiment, a nanoparticle delivery vehicle of the present invention can comprise a plurality of different sequences or "keys," which can enable a given nanoparticle delivery vehicle to pass through various potential barriers to translocation.

Another advantage of a preferred embodiment of the nanoparticle delivery vehicles of the present invention is the ability to create nanoparticles that comprise a material that is biologically inert. For example, it is possible to fashion nanoparticles from gold and other materials. Gold, unlike some other materials, is biologically inert and can be physiologically tolerated without significant adverse effects by biological systems. Further, a nanoparticle can comprise biodegradable material, which upon breakdown, can yield the nanoparticle delivery vehicle's component parts, all of which are themselves biodegradable.

Yet another advantage of a preferred embodiment of the nanoparticle delivery vehicles of the present invention is their ability to function in any of a variety of roles, due to the lack of restriction on the active agent. A nanoparticle delivery vehicle of the present invention can therefore fill a variety of roles by simply changing the active agent to suit the need. Thus, a nanoparticle delivery vehicle designed to modulate gene expression by delivering an antisense strand to the nucleus of a cell can also function as a transcription factor decoy by replacing the antisense strand active agent with a double stranded sequence of DNA.

Finally, the size of the nanoparticle can be varied, which can provide for differential targeting of a nanoparticle delivery vehicle. Nanoparticle size can influence the targeting of a delivery vehicle. A nanoparticle delivery vehicle comprising a nanoparticle of about 30 nm or larger will not be transported into the nucleus of a cell and will remain in the cytoplasm of the cell, even if an NLS is present. However, although such a nanoparticle delivery vehicle might not be transported to the nucleus of a cell, the nanoparticle delivery vehicle can be internalized by the cell and remain localized in the cytoplasm. Thus, such vehicles can be useful for modulating processes occurring in the cytoplasm, such as translation and translocation.

Laboratory Example

The following Laboratory Example has been included to illustrate preferred modes of the invention. Certain aspects of the following Laboratory Example are described in terms of techniques and procedures found or contemplated by the present inventors to work well in the practice of the invention. This Laboratory Example are exemplified through the use of standard laboratory practices of the inventors. In light of the present disclosure and the general level of skill in the art, those of skill will appreciate that the following Laboratory Example is intended to be exemplary only and that numerous changes, modifications and alterations can be employed without departing from the spirit and scope of the present invention.

Laboratory Example

Targeted entry into cells is an increasingly important area of research. The nucleus is a desirable target since the genetic information of the cell and transcription machinery resides there. The diagnoses of disease phenotype, the identification of potential drug candidates, and the treatment of disease by novel methods such as antisense therapy would be enhanced greatly by the efficient transport of materials to living cell nuclei (Kole & Sazani, (2001) Curr. Opin. Mol. Ther. 3: 229-234). The intracellular fate of gold nanoparticles chemically designed to transit from outside a living cell into the nucleus is reported in the present Laboratory Example.

Although metal, semiconductor, polymer, and magnetic particles have been introduced into cells previously (Liu et al., (2001) Biomacromolecules 2: 362-368; Marinakos et al., (2001) J. Phys. Chem. B. 105: 8872-8876; West & Halas, (2000) Curr. Opin. Biotech. 11: 215-217; Hogemann et al., (2002) Bioconjugate Chem. 13: 116-121), there is no comprehensive cytochemical approach to targeting the nucleus from outside the plasma membrane of living cells. The development of an approach that permits the transport of nanometer-sized particles into cells has important applications in cell biology as a tool for the study of cell development and differentiation.

A number of techniques have been used previously to determine cellular trajectories of particles. Indeed, the use of electron microscopy with colloidal gold stains was perhaps the first modern method of cell structure characterization (Havat (Ed.), (1998) Colloidal Gold. Principles, Methods, and Applications; Academic Press, Inc.: San Diego, Vol. 1). More recently, fluorescence microscopy has been used to locate fluorophores, including luminescent CdSe nanoparticles in cells (Bruchez et al., (1998) Science 281: 2013-2016; Nie & Chan, (1998) Science 281: 2016-2018). However, prior studies of nuclear translocation of nanoparticles were performed using microinjection or chemically modified cells, thus bypassing cellular membrane entry. The combination of targeted endocytosis coupled with nuclear uptake has not been demonstrated in a nanoparticle vector using intact cells, prior to the present disclosure.

Targeted nuclear delivery is a challenging task, as any cell-specific nuclear probe must satisfy minimally the following requirements (Hallenbeck & Stevenson, (2000) Targetable Gene Delivery Vectors (Habib, Ed.), Kluwer Academic/Plenum Publishers: New York, pp 37-46): it must (i) be small enough to enter the cell and cross the nuclear membrane; (ii) bind to cell-specific plasma membrane receptors by receptor-mediated endocytosis (RME), for example; (iii) escape endosomal/lysosomal pathways; (iv) pass through the nuclear pore complex, and (v) have low toxicity. In the present Laboratory Example, results of intracellular trafficking studies of nanoparticles designed to perform these and other functions are reported.

A nanoparticle vector of the present Laboratory Example comprises a core of a 20 nm gold particle and a shell of bovine serum albumin (BSA) conjugated to various cellular targeting peptides, which are presented in the following Table of Representative Peptide Sequences:

Table of Representative Peptide Sequences

| Peptide | Sequence | SEQ ID NO | Source | Peptide/BSA |
|---------|----------|-----------|--------|-------------|
| N0 | CGGGPKKKRKVGG | 3 | SV40 large T NLS | 7 ± 1 |
| N1 | CGGFSTSLRARKA | 4 | Adenoviral NLS | 8 ± 1 |
| N2 | CKKKKKKSEDEYPYVPN | 5 | Adenoviral RME | 9 ± 2 |
| N3 | CKKKKKKKSEDEYPYVPNFSTSLRARKA | 6 | Adenoviral Fiber Protein | 6 ± 2 |

When preparing the peptides disclosed in the Table of Representative Peptide Sequences, peptides were conjugated to BSA with a 3-maleimido benzoic acid N-hydroxysuccinimide ester linker. Gel electrophoresis (SDS-PAGE and IEF) was used to quantify peptide:BSA ratio. Each peptide was chosen to perform a certain task (e.g., RME). Individual peptides have been explored previously as therapeutic delivery vectors (Morris et al., (2000) Curr. Opin. Biotech. 11: 461-466). However, highly efficient nuclear targeting in biology is accomplished by viruses, which utilize different peptides for each barrier mentioned above. A significant observation of the present Laboratory Example is that viral peptides conjugated to proteins on the surface of a nanoparticle retain their function of promoting cell entry and nuclear targeting. Moreover, separate short peptides on a single particle lead to more efficient nuclear targeting than a single long peptide. Together the gold core and multifunctional peptide shell provides a flexible scaffold that can be tuned to target specific cells for intranuclear assays or therapeutic delivery.

Gold was chosen as an intracellular targeting vector primarily for three reasons. First, gold can be routinely synthesized in sizes varying continuously from 0.8 nm to 200 nm with <5% size dispersity. Secondly, gold can be modified with a large collection of small molecules, peptides, proteins, DNA, and polymers. Moreover, all of these functional elements can be combined on a single particle, often via simple one-pot procedures. Finally, gold particles have strong visible light extinctions that can be used to monitor their trajectories inside cells under polarized light conditions. These properties were advantageously employed in a novel combination of video-enhanced color (VEC) microscopy and differential interference contrast microscopy (DIC), which facilitated the observation of the trajectory of 20 nm gold nanoparticles inside cells.

Dynamic light scattering and transmission electron microscopy revealed that BSA-peptide conjugates add <2 nm to the radius of the nanoparticle complex. The fact that BSA does not add greatly to the size of the gold particle is important in its use in constructing nuclear targeting vectors because the diameter of the nuclear pore complex is 20-50 nm depending on the cell line (Feldherr & Akin, (1990) J. Cell Biol. 111:1-8). The 20 nm gold particles used in he present Laboratory Example have a maximum diameter of 25 nm when complexed with any of the BSA-peptide conjugates studied (see Supporting Information).

Nuclear translocation through the nuclear pore complex has previously been studied using gold nanoparticles labeled with an NLS from SV-40 virus (large T antigen). In the classic studies nuclear targeting was observed by transmission electron microscopy (TEM) following microinjection into the cell (Feldherr et al., (1992) Proc. Nat. Acad. Sci. U.S.A. 89: 11002-11005). As a test case, nanoparticle complexes comprising peptide N0 were introduced into the growth medium of HepG2 cells. Surprisingly, N0 complexes were observed inside the cytoplasm of HepG2 cells, however N0 did not enter the nucleus. Experiments at 4° C. indicated that cell entry was via an energy-dependent pathway. This observation suggests that N0 entered the cell by receptor-mediated endocytosis, but was unable to escape the endosome and target the nucleus (TEM and confocal fluorescence microscopy confirmed that nanoparticles were confined to endosomes). These results highlight the challenges associated with nuclear targeting: although a known NLS peptide is able to enter HepG2 cells, it cannot target the nucleus unless it is capable of endosomal escape.

In an effort to enhance nuclear targeting efficiency in HepG2 cells, peptides from the adenovirus were explored. The adenovirus is widely used in gene delivery and there is a great deal of interest in replacing the whole virus, which is potentially infectious and immunogenic, with peptide sequences derived from the adenovirus fiber protein (Seth, (2000) Adenoviral Vectors; (Habib, Ed.) Kluwer Academic/Plenum Publishers: New York, pp 13-22; Bilbao et al., (1998) Targeted Adenoviral vectors for Cancer Gene Therapy, Plenum Press: New York, Vol. 57, pp 365-374). This protein is known to contain both RME and NLS sequences (N1 and N2, in the Table of Representative Peptide Sequences). The full length fiber containing both the RME and NLS is peptide N3 in the Table of Representative Peptide Sequences. A comparison of the functions of these targeting peptides when complexed to a gold nanoparticle is as follows. N1 does not enter the cell. N2 enters the cell, but remains trapped in endosomes and does not reach the nucleus. N3 targets the nucleus, however, N1/N2 has a greater propensity for nuclear targeting than N1, N2, or N3. These results are interpreted as follows. N1 presents only the adenovirus NLS (Table of Representative Peptide Sequences). This peptide does not function as an RME and has no other chemical moiety that permits cell entry. N2 presents the RME (NPXY (SEQ ID NO: 7) motif) and it enters the cell, however, it is not capable of nuclear targeting (Chen et al., (1990) J. Biol. Chem. 265: 3116-3123).

These results show that the nanoparticle complex must present both RME and NLS in order to both enter the cell and achieve nuclear localization. The VEC-DIC results clearly show significant numbers of N3 in the nucleus in agreement with a gene delivery study using this peptide (Zhang et al., (1999) *Gene Ther.* 6: 171-181). The N1/N2-labeled nanoparticle is even more efficient, as seen by VEC-DIC microscopy.

Another comparison to be made is between a multifunctional nanoparticle N1/N2 that presents the RME and NLS on separate BSA bioconjugates and N3, which presents the full-length adenoviral fiber peptide. N1/N2 was present in the nucleus in greater numbers than N3. The origin of the higher nuclear targeting efficiency in particles carrying two short peptides versus one long sequence could be structural or spatial. Infrared spectroscopy indicates that all peptides employed in this Exa,[;e adopt an extended confirmation when attached to nanoparticles. However, when one long peptide is synthesized with two consecutive signals, it is likely that one of the signals will be less accessible to cellular receptors. This is important for NPXY (SEQ ID NO: 7) motifs, for example, since tandem interaction of two NPXY (SEQ ID NO: 7) regions has been shown to facilitate RME (Hussain, (2001) *Front. Biosci.* 6: 417-428). Attaching the two-peptide signals to a nanoparticle as separate, shorter pieces likely gives them equal access to cellular receptors.

The methods used here provide an approach for rapidly assessing the efficacy of various combinations of targeting peptides using nanoparticle complexes for nuclear targeting. The VEC-DIC combination microscopy permits examination of hundreds of samples per day, an improvement over costly and time consuming electron and confocal microscopy techniques.

The multifunctional approach demonstrated using adenoviral targeting sequences provides a test of the function of individual peptide sequences that will permit effective and cell-specific targeting for a range of scientific and medical applications.

REFERENCES

The references listed below as well as all references cited in the specification are incorporated herein by reference to the extent that they supplement, explain, provide a background for or teach methodology, techniques and/or compositions employed herein.

Agrawal, (1996) *Trends Biotechnol.* 14(10): 376-87
*Antisense Therapeutics*, (1996) (Agrawal, ed.), Humana Press, Totowa, N.J.
Autieri & Agrawal, (1998) *J. Biol. Chem.* 273: 14731-37
Bassell et al., (1999) *FASEB J.* 13: 447-54
Bilbao et al., (1998) *Targeted Adenoviral vectors for Cancer Gene Therapy*, Plenum Press: New York, Vol. 57, pp 365-374
Bruchez et al., (1998) *Science* 281: 2013-2016
Calabretta et al., (1996) *Semin. Oncol.*, 23: 78-87
Chakhmakhcheva et al., (1999) *Nucleos. Nucleot.* 18: 1427-28
Chen et al., (1990) *J. Biol. Chem.* 265: 3116-3123
*Colloidal Drug Delivery Systems*, (1994) (Kreuter, ed.), Marcel Dekker, Inc., New York, pp. 219-342
Couvreur et al., (1982) *J. Pharm. Sci.* 71: 790-92
Couvreur et al., (1986) in *Polymeric Nanoparticles and Microspheres*, (Guiot & Couvreur, eds.), CRC Press, Boca Raton, pp. 27-93
DeVita, (1983) in *Harrison's Principles of Internal Medicine*, McGraw-Hill Book Co., New York, p.68
Enustun & Turkevich, (1963) *J. Am. Chem. Soc.* 85: 3317
Feldherr & Akin, (1990) *Electron Microsc. Rev.* 3(1): 73-86
Feldherr & Akin, (1990) *J. Cell Biol.* 111:1-8
Feldherr & Akin, (1994) *Exp. Cell Res.* 215:206-10
Feldherr & Akin, (1999) *J. Cell Sci.* 112:2043-48
Feldherr et al., (1992) *Proc. Nat. Acad. Sci. U.S.A.* 89: 11002-11005
Gabe, (1994) *Radiother. Oncol.* 30:199-205
Hainfeld & Furuya, (1992) *J. Histochem. Cytochem.* 40: 177-84
Hainfeld, (1992) *Proc. Natl. Acad. Sci. USA* 89:11064-11068
Hainfeld, (1992) *Ultramicroscopy* 46: 135-44
Hallenbeck & Stevenson, (2000) *Targetable Gene Delivery Vectors* (Habib, Ed.), Kluwer Academic/Plenum Publishers: New York, pp 37-46
Hayashi, (1987) *Physics Today*, December 1987, pp. 44-60
Hayashi, (1987) *Vac. Sci. Technol.* July/August 1987, A5(4): 1375-84
Hayat (Ed.), (1998) *Colloidal Gold. Principles, Methods, and Applications;* Academic Press, Inc.: San Diego, Vol. 1
Hogemann et al., (2002) *Bioconjugate Chem.* 13: 116-121)
Hussain, (2001) *Front. Biosci.* 6: 417-428
Kole & Sazani, (2001) *Curr. Opin. Mol. Ther.* 3: 229-234
Kreuter, (1994) *Eur. J Drug Metab. Ph.* 3: 253-56
Labhasetwar et al., (1997) *Adv. Drug. Del. Rev.,* 24: 63-85
Ledley, (1993) *Clin. Invest. Med.* 16: 78-88
Lefebvre-D'Hellencourt et al., (1995) *Eur. Cytokine Netw.,* 6: 7-19
Lev-Lehman et al., (1997) in *Antisense Therapeutics,* (Cohen & Smisek, eds.), Plenum Press, New York
Liu et al., (2001) *Biomacromolecules* 2: 362-368
Magin et al., (2000) *Virology* 274: 11-16
Maniatis et al., (1987) *Science,* 236: 1237-45
Marinakos et al., (1998) *Chem. Mater.* 10: 1214-19
Marinakos et al., (1999) *Adv. Mater.* 11: 34-37
Marinakos et al., (2001) *J. Phys. Chem. B.* 105: 8872-8876
Moede et al., (1999) *FEBS Lett.* 461:229-34
Morris et al., (2000) *Curr. Opin. Biotech.* 11: 461-466
*MRS Bulletin*, January 1990, pgs. 16-47
Mullin et al., (1997) *J. Biol. Chem.* 272: 5668-81
Nie & Chan, (1998) *Science* 281: 2016-2018
Norden et al., (2000) *FASEB J.* 14(9): 1041-60
*Oligonucleotide & Gene Therapy-Base Antisense Therapeutics,* (1997), (Mori, ed.), Drug & Market Development Publications
*Protein Purification Applications: A Practical Approach,* (1989) (Harris & Angal, eds.) IRL Press, Oxford, England
*Protein Purification: Principles, High Resolution Methods, Applications,* (1989) (Janson & Ryden, eds.) VCH Publishers, New York
*Remington's Pharmaceutical Sciences,* (1980) (Osol, ed.) 16th Ed., Mack Publishing Company, Easton, Pa.
Sambrook et al., (1992) *Molecular Cloning: A Laboratory Manual,* Cold Spring Harbor, N.Y.
Seth, (2000) *Adenoviral Vectors*; (Habib, Ed.) Kluwer Academic/Plenum Publishers: New York, pp 13-22
Tinland et al., (1992) *Proc. Natl. Acad. Sci. U.S.A.* 89: 7442-46
U.S. Pat. No. 5,783,263
U.S. Pat. No. 6,106,798
West & Halas, (2000) *Curr. Opin. Biotech.* 11: 215-217
Wu & Wu, (1991) *Biotherapy* 3: 87-95
Zhang et al., (1999) *Gene Ther.* 6: 171-181

It will be understood that various details of the invention can be changed without departing from the scope of the invention. Furthermore, the foregoing description is for the purpose of illustration only, and not for the purpose of limitation—the invention being defined by the claims.

What is claimed is:

1. A nanoparticle delivery vehicle for contacting a target cell and crossing a cellular membrane and a nuclear membrane of a target cell, the nanoparticle delivery vehicle comprising:
   (a) a nanoparticle, wherein the nanoparticle comprises a material selected from the group consisting of cadmium selenide, titanium, titanium dioxide, tin, tin oxide, silicon, silicon dioxide iron, iron$^{III}$ oxide, silver, nickel, gold, copper, aluminum, steel, cobalt-chrome alloy, titanium alloy, brushite, tricalcium phosphate, alumina, silica, zirconia, diamond, polystyrene, silicone rubber, polycarbonate, polyurethanes, polypropylenes, polymethylmethaacrylate, polyvinyl chloride, polyesters, polyethers, and polyethylene;
   (b) an active agent;
   (c) a nuclear localization signal; and
   (d) one or more extracellular targeting agents, wherein the one or more extracellular targeting agents is recognized and bound by one or more receptors on a surface of a target cell.

2. The nanoparticle delivery vehicle of claim 1, wherein the nanoparticle is biodegradable.

3. The nanoparticle delivery vehicle of claim 1, wherein the nanoparticle ranges from about 1 nm to about 1,000 nm in diameter.

4. The nanoparticle delivery vehicle of claim 1, wherein the nanoparticle is about 30 nm or less in diameter.

5. The nanoparticle delivery vehicle of claim 1, wherein the active agent is selected from the group consisting of oligomers of double stranded nucleic acids, single stranded nucleic acids, chemically modified nucleic acids, peptide nucleic acids, proteins and small molecules.

6. The nanoparticle delivery vehicle of claim 1, further comprising a tether sequence attached to, and disposed between, the active agent and the nanoparticle.

7. The nanoparticle delivery vehicle of claim 1, wherein the nanoparticle delivery vehicle is disposed in a pharmaceutically acceptable diluent.

8. The nanoparticle delivery vehicle of claim 1, further comprising a detectable moiety.

9. The nanoparticle delivery vehicle of claim 8, wherein the detectable moiety is a fluorescent compound.

10. The nanoparticle delivery vehicle of claim 1, wherein each sequence is independently associated with the nanoparticle.

11. The nanoparticle delivery vehicle of claim 1, wherein the extracellular targeting agent is an RME motif.

12. The nanoparticle delivery vehicle of claim 1, wherein the extracellular targeting agent is selected from the group consisting of diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, IgE, polymeric IgA, maternal IgG, insulin, epidermal growth factor, growth hormone, thyroid stimulating hormone, nerve growth factor calcitonin, glucagon, prolactin, luteinizing hormone, thyroid hormone, platelet derived growth factor, interferon, nuclear localization signal and catecholamines.

13. The nanoparticle delivery vehicle of claim 1, wherein the extracellular targeting agent comprises a fragment of a molecule selected from the group consisting of diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, IgE, polymeric IgA, maternal IgG, insulin, epidermal growth factor, growth hormone thyroid stimulating hormone, nerve growth factor, calcitonin, glucagon, prolactin, luteinizing hormone, thyroid hormone, platelet derived growth factor, interferon and catecholamines.

14. The nanoparticle delivery vehicle of claim 1, further comprising two or more different active agents.

15. The nanoparticle delivery vehicle of claim 1, further comprising a biocompatibility-enhancing agent.

16. The nanoparticle delivery vehicle of claim 1, further comprising a protective coating covering at least part of the delivery vehicle.

17. The nanoparticle delivery vehicle of claim 16, further comprising a protective coating covering the entire delivery vehicle.

18. The nanoparticle delivery vehicle of claim 16, wherein the protective coating comprises a polymer.

19. The nanoparticle delivery vehicle of claim 16, wherein the protective coating comprises a biological material.

20. The nanoparticle delivery vehicle of claim 16, wherein the biological material is a protein, lipid, carbohydrate, or combination thereof.

21. A nanoparticle delivery vehicle for contacting a target cell and crossing a cellular membrane and a nuclear membrane of a target cell, the nanoparticle delivery vehicle comprising:
(a) a nanoparticle, wherein the nanoparticle comprises a material selected from the group consisting of cadmium selenide, titanium, titanium dioxide, tin, tin oxide, silicon, silicon dioxide, iron, iron$^{III}$ oxide, silver, nickel, gold, copper, aluminum, steel, cobalt-chrome alloy, titanium alloy. brushite, tricalcium phosphate, alumina, silica, zirconia, diamond, polystyrene, silicone rubber, polycarbonate, polyurethanes, polypropylenes, polymethylmethaacrylate, polyvinyl chloride, polyesters, polyethers, and polyethylene;
(b) an active agent;
(c) a nuclear localization signal; and
(d) one or more extracellular targeting agents, wherein the one or more extracellular targeting agents is recognized and bound by one or more receptors on a surface of a target cell;
wherein the nuclear localization signal or one of the one or more extracellular targeting agents is selected from the group consisting of SEQ ID NOs: 4-6, and combinations thereof.

22. A nanoparticle delivery vehicle for contacting a target cell and crossing a cellular membrane and a nuclear membrane of a target cell, the nanoparticle delivery vehicle comprising:
(a) a nanoparticle, wherein the nanoparticle comprises a material selected from the group consisting of cadmium selenide, titanium, titanium dioxide, tin, tin oxide, silicon, silicon dioxide, iron, iron$^{III}$ oxide, silver, nickel, gold, copper, aluminum, steel, cobalt-chrome alloy, titanium alloy, brushite, tricalcium phosphate, alumina, silica, zirconia, diamond, polystyrene, silicone rubber, polycarbonate, polyurethanes, polypropylenes, polymethylmethaacrylate, polyvinyl chloride, polyesters, polyethers, and polyethylene;
(b) an active agent;
(c) a nuclear localization signal; and
(d) one or more extracellular targeting agents, wherein the one or more extracellular targeting agents is recognized and bound by one or more receptors on a surface of a target cell;
wherein the nuclear localization signal comprises SEQ ID NO: 4 and one of the one or more extracellular targeting agents comprises SEQ ID NO: 5.

23. The nanoparticle delivery vehicle of claim 22, wherein the target cell is a human hepatocarcinoma cell.

24. A nanoparticle delivery vehicle for contacting a target cell and crossing a cellular membrane and a nuclear membrane of a target cell, the nanoparticle delivery vehicle comprising:
(a) a nanoparticle, wherein the nanoparticle comprises a material selected from the group consisting of cadmium selenide, titanium, titanium dioxide, tin, tin oxide, silicon, silicon dioxide, iron, iron$^{III}$ oxide, silver, nickel, gold, copper, aluminum, steel, cobalt-chrome alloy, titanium alloy, brushite, tricalcium phosphate, alumina, silica, zirconia, diamond, polystyrene, silicone rubber, polycarbonate, polyurethanes. polypropylenes, polymethylmethaacrylate, polyvinyl chloride, polyesters, polyethers, and polyethylene;
(b) an active agent;
(c) a nuclear localization signal; and
(d) one or more extracellular targeting agents, wherein the one or more extracellular targeting agents is recognized and bound by one or more receptors on a surface of a target cell;
wherein the nuclear localization signal and one of the one or more extracellular targeting agents together comprise SEQ ID NO: 6.

25. The nanoparticle delivery vehicle of claim 24, wherein the target cell is a human hepatocarcinoma cell.

26. A nanoparticle delivery vehicle for contacting a target cell and crossing a cellular membrane and a nuclear membrane of a target cell, the nanoparticle delivery vehicle comprising:
(a) a nanoparticle;
(b) an active agent;
(c) a nuclear localization signal; and
(d) one or more extracellular targeting agents, wherein the one or more extracellular targeting agents is recognized and bound by one or more receptors on a surface of a target cell;
wherein the nuclear localization signal or one of the one or more extracellular targeting agents is selected from the group consisting of SEQ ID NOs: 4-6, and combinations thereof.

* * * * *